US011224853B2

(12) United States Patent
Harp et al.

(10) Patent No.: US 11,224,853 B2
(45) Date of Patent: Jan. 18, 2022

(54) METAL SUPPORTED POWDER CATALYST MATRIX AND PROCESSES FOR MULTIPHASE CHEMICAL REACTIONS

(71) Applicant: W.L. Gore & Associates, Inc., Newark, DE (US)

(72) Inventors: Gary P. Harp, Newark, DE (US); Jeffrey A. Knopf, Jr., Wilmington, DE (US); William J. Napier, III, Thorndale, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 17/043,882

(22) PCT Filed: Apr. 11, 2018

(86) PCT No.: PCT/US2018/027020
§ 371 (c)(1),
(2) Date: Sep. 30, 2020

(87) PCT Pub. No.: WO2019/199294
PCT Pub. Date: Oct. 17, 2019

(65) Prior Publication Data
US 2021/0031163 A1    Feb. 4, 2021

(51) Int. Cl.
*B01J 10/00* (2006.01)
*B01J 19/24* (2006.01)
(Continued)

(52) U.S. Cl.
CPC ......... *B01J 19/1893* (2013.01); *B01J 10/007* (2013.01); *B01J 19/0066* (2013.01);
(Continued)

(58) Field of Classification Search
CPC .. B01J 10/007; B01J 19/1893; B01J 19/1868; B01J 19/0066; B01J 31/06; B01J 35/065
See application file for complete search history.

(56) References Cited

U.S. PATENT DOCUMENTS

| 3,864,124 A | 2/1975 | Breton et al. |
| 3,953,566 A | 4/1976 | Gore |

(Continued)

FOREIGN PATENT DOCUMENTS

| CA | 3005270 | 8/2017 |
| CN | 1159437 | 9/1997 |

(Continued)

OTHER PUBLICATIONS

Bengtson et al., "Catalytic membrane reactor to simultaneously concentrate and react organics" Chemical Engineering Journal 85 (2002), pp. 303-311.

(Continued)

*Primary Examiner* — Lessanework Seifu
(74) *Attorney, Agent, or Firm* — Amy L. Miller

(57) ABSTRACT

A catalytic membrane composite that includes porous supported catalyst particles durably enmeshed in a porous fibrillated polymer membrane is provided. The porous fibrillated polymer membrane may be manipulated to take the form of a tube, disc, or diced tape and used in multiphase reaction systems. The supported catalyst particles are composed of at least one finely divided metal catalyst dispersed on a porous support substrate. High catalytic activity is gained by the effective fine dispersion of the finely divided metal catalyst such that the metal catalyst covers the support substrate and/or is interspersed in the pores of the support substrate. In some embodiments, the catalytic membrane composite may be introduced to a stirred tank autoclave reactor system, a continuous flow reactor system, or a Parr (Continued)

Shaker reaction system and used to effect the catalytic reaction.

12 Claims, 13 Drawing Sheets

(51) Int. Cl.
    *B01J 19/18*     (2006.01)
    *B01J 19/00*     (2006.01)
    *B01J 31/06*     (2006.01)
    *B01J 35/06*     (2006.01)
    *C07C 209/36*     (2006.01)

(52) U.S. Cl.
    CPC .......... *B01J 19/1868* (2013.01); *B01J 31/06* (2013.01); *B01J 35/065* (2013.01); *C07C 209/36* (2013.01); *B01J 2231/641* (2013.01); *B01J 2531/002* (2013.01)

(56) References Cited

U.S. PATENT DOCUMENTS

| | | | |
|---|---|---|---|
| 4,096,227 A | 6/1978 | Gore | |
| 4,224,185 A | 9/1980 | Wriseters | |
| 4,478,665 A | 10/1984 | Hubis | |
| 4,985,296 A | 1/1991 | Mortimer, Jr. | |
| 5,620,669 A | 4/1997 | Plinke et al. | |
| 5,645,626 A | 7/1997 | Edlund et al. | |
| 5,708,044 A | 1/1998 | Branca | |
| 5,849,235 A | 12/1998 | Sassa et al. | |
| 5,891,402 A | 4/1999 | Sassa et al. | |
| 6,218,000 B1 | 4/2001 | Rudolf et al. | |
| 6,331,351 B1 | 12/2001 | Waters et al. | |
| 6,514,627 B1 | 2/2003 | Heil et al. | |
| 6,521,019 B2 | 2/2003 | Jain et al. | |
| 6,541,589 B1 | 4/2003 | Baillie | |
| 7,531,611 B2 | 5/2009 | Sabol et al. | |
| 8,114,289 B2 | 2/2012 | Zheng et al. | |
| 8,637,144 B2 | 1/2014 | Ford | |
| 8,974,739 B2 | 3/2015 | Yoshida | |
| 9,139,669 B2 | 9/2015 | Xu et al. | |
| 9,289,741 B2 | 3/2016 | TeGrotenhuis et al. | |
| 2003/0205131 A1 | 11/2003 | Golden et al. | |
| 2005/0057888 A1 | 3/2005 | Mitchell et al. | |
| 2010/0119699 A1 | 5/2010 | Zhong et al. | |
| 2013/0143326 A1 | 6/2013 | Tai et al. | |
| 2014/0008210 A1 | 1/2014 | Guia et al. | |
| 2015/0376095 A1 | 12/2015 | Edgar et al. | |
| 2016/0032069 A1 | 2/2016 | Sbriglia | |
| 2016/0136914 A1 | 5/2016 | Sbriglia et al. | |

FOREIGN PATENT DOCUMENTS

| | | |
|---|---|---|
| CN | 106110762 | 11/2016 |
| EP | 1336428 | 8/2003 |
| GB | 2015543 | 9/1979 |
| KR | 20150124066 A | 11/2015 |
| WO | WO2008/115791 | 9/2008 |
| WO | WO2010/066676 | 6/2010 |
| WO | WO2011/121797 | 10/2011 |
| WO | WO2013/121593 | 8/2013 |
| WO | WO2017106730 | 6/2017 |

OTHER PUBLICATIONS

Bengtson and Fritsch, "Catalytic membrane reactor for the selective hydrogenation of edible oil: platinum versus palladium catalyst" Desalination 200 (2006) pp. 666-667.

Brandão et al., "Propyne hydrogenation in a continuous polymeric catalytic membrane reactor" Chemical Engineering Science 62 (2007) pp. 6768-6776.

Dittmeyer et al., "A review of catalytic membrane layers for gas/liquid reactions", Topics in Catalysis, May 2004, vol. 29, Nos. 1-2. pp. 3-27.

Greene et al., "PTFE-Membrane Flow Reactor for Aerobic Oxidation Reactions and Its Application To Alcohol Oxidation" Organic Process Research & Development. 2015, 19, pp. 858-864.

Morris et al. "Photocatalytic membrane for removal of organic contaminants during ultra-purification of water", Clean Tech Environ Policy 6 (2004) pp. 96-104.

O'Brien et al. "Hydrogenation in flow: Homogenous and heterogeneous catalysis using Teflon AF-2400 to effect gas liquid contact at elevated pressure" Chemical Science, 2011, 2, pp. 1250-1257.

Ozdemir et al., "Catalytic polymeric membranes: Preparation and application", Applied Catalysis A: General 307 (2006) pp. 167-183.

Schmidt et al., "Selectivity of partial hydrogenation reactions performed in a pore-through-flow catalytic membrane reactor" Catalysis Today 104 (2005) pp. 305-312.

Stanford et al, "Aqueous phase Hydrogenation of levulinic acid using a porous catalytic membrane reacotr" Catalysis Today 268 (2016) pp. 19-28.

Stankiewicz, A., 2010, "Multiphase Reactors" in Chemical Engineering and Chemical Process Technology, vol. III, Encyclopedia of Life Support Systems (EOLSS) Publishers, Paris France. 8 pgs.

Vankelecom, I. "Polymeric Membranes in Catalytic Reactors" Chem. Rev. 2002, 102, pp. 3779-3810.

Ziegler et al., "Palladium modified porous polymeric membranes and their performance in selective hydrogenation of propyne" Journal of Membrane Science 187 (2001) pp. 71-84.

METAL SUPPORTED POWDER CATALYST MATRIX AND PROCESSES FOR MULTIPHASE CHEMICAL REACTIONS

FIELD

The present disclosure relates generally to multiphase chemical reactions, and more specifically, to a porous fibrillated polymer membrane that includes supported catalyst particles durably enmeshed within a porous fibrillated polymer membrane for use in multiphase reaction systems.

BACKGROUND

Multiphase chemical reaction systems and processes utilizing powdered catalysts as the solid phase are known in the art. However, three phase gas-liquid-solid reactions present some difficult problems. One difficulty is that of obtaining substantially uniform dispersion or mixing of gas and liquid with the solid for reaction. Sometimes, when affecting these reactions, gas and liquid are introduced mixed but separate or de-mix before reaching the solid catalyst surface. As a result, side reactions often occur causing by-product buildup and possibly, dangerous conditions. Poor conversion is another aspect of improper mixing. Two phase catalytic reactions are also challenging for solid catalyst mixing.

The most common current solution to the problems associated with multiphase chemical reactions is to slurry a finely divided powdered catalyst in the liquid phase using a shaft driven impeller mixer as it provides for easy mixing and high distribution of catalyst surface area over the liquid volume. However, these finely divided powdered catalysts often require extensive operator handling during reactor charging and during filtration to separate the catalyst and products after reaction. Additionally, due to their fine size, they are prone to transfer losses as they stick to surfaces and in crevices at seals within the reactor. Catalyst remaining in the reactor can also lead to process safety concerns. For example, the remaining catalyst may become dry and cause a fire or explosion. Further, the transfer loss of the powdered catalyst results in inferior net productivity. Operability challenges are also present with the use of powdered catalysts, as extensive careful operator handling is required to prevent ignition of dry catalyst powder on reactor charging.

SUMMARY

One embodiment relates to a reaction system for multiphase reactions having at least three phases where the reaction system includes (1) a stirred tank reaction vessel including a rotatable impeller shaft having thereon at least one impeller blade where the rotatable impeller shaft is rotatably affixed to a catalytic article, (2) a liquid phase including at least one liquid phase reactant, and (3) a gas phase comprising at least one gas phase reactant. The catalytic article includes supported catalyst particles durably enmeshed within the porous fibrillated polymer membrane. The porous fibrillated polymer membrane may be in the form of an immobilized catalyst disc or disc stack. In at least one embodiment, the disc stack comprises a plurality of immobilized catalyst discs with intervening spacers separating the immobilized catalyst discs. Also, the immobilized catalyst discs have therein through-holes for circulation of a reaction mixture through the disc stack. In one exemplary embodiment, the impeller blade is pitched. The reaction system may be configured for hydrogenation. In exemplary embodiments, the reaction system is a stirred tank autoclave reactor system. The porous fibrillated polymer membrane may include polytetrafluoroethylene (PTFE), expanded polytetrafluoroethylene (ePTFE), modified PTFE, or a PTFE copolymer. Further, the catalytic article is not configured as a contactor. In an alternate embodiment, the porous fibrillated polymer membrane be in the form of diced tape.

Another embodiment relates to a continuous flow reaction system for multiphase reactions having at least three phases where the reaction system includes (1) a catalytic article including a porous fibrillated polymer membrane that includes supported catalyst particles durably enmeshed within the porous fibrillated polymer membrane, (2) a liquid phase comprising at least one liquid phase reactant, (3) a gas phase comprising at least one gas phase reactant, and (4) a reaction vessel configured for continuous flow of the liquid phase reactant and the gas phase reactant across and through the catalytic article. The catalytic article may be in the form of a tube or a plurality of tubes bundled in a tubular array. In an alternate embodiment, the catalytic article may be in the form of diced tape. In at least one embodiment, the reaction system is configured for hydrogenation. The porous fibrillated polymer membrane may include polytetrafluoroethylene (PTFE), expanded polytetrafluoroethylene (ePTFE), modified PTFE, or a PTFE copolymer. Additionally, the porous fibrillated has a porosity from about 30% to about 95%. Further, the catalytic article is not configured as a contactor.

Yet another embodiment relates to a continuous flow reaction system for multiphase reactions having at least three phases where the reaction system includes (1) a catalytic article including a porous fibrillated polymer membrane that includes supported catalyst particles durably enmeshed within the porous fibrillated polymer membrane where the catalytic article is in the form of diced tape, (2) a reaction mixture including a liquid phase having at least one reactant and a gas phase having at least one additional reactant, (3) a reaction vessel containing the catalytic article and reaction mixture. The reaction mixture has free access to move through and around the catalytic particles to affect a hydrogenation reaction. The porous fibrillated polymer membrane may include polytetrafluoroethylene (PTFE), expanded polytetrafluoroethylene (ePTFE), modified PTFE, or a PTFE copolymer. The porous fibrillated polymer membrane is insoluble to reactants and products in the multiphase chemical reaction. Further, the catalytic article is not configured as a contactor.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
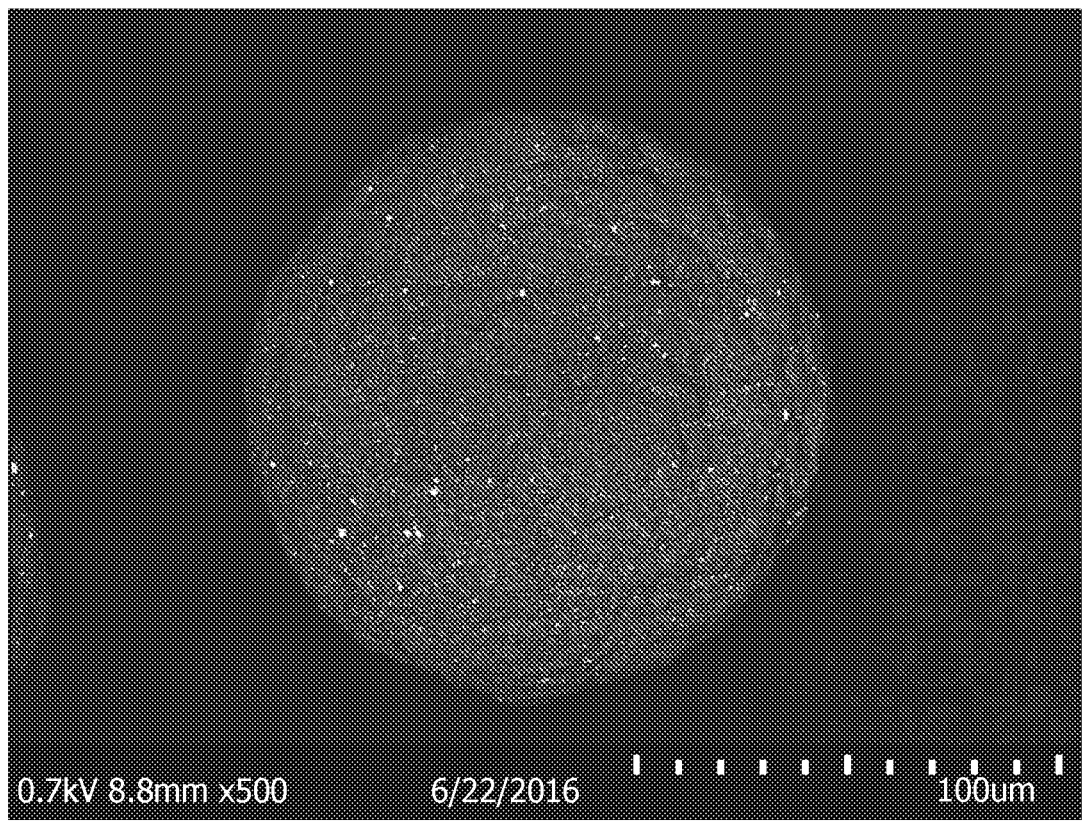
FIG. 1 is a scanning electron micrograph (SEM) of an exemplary supported catalyst particle with a finely divided metal on its surface in accordance with at least one embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting. As used herein, the terms "porous supported catalyst particle" and "supported catalyst particle" may be used interchangeably herein. Also, the terms "immobilized catalyst disc" and "disc" may be used interchangeably herein.

The present disclosure is directed to a catalytic membrane composite that comprises porous supported catalyst particles durably enmeshed in a porous fibrillated polymer membrane. It is to be noted that the supported catalyst particles may alternatively be non-porous or substantially non-porous. The fibrillated polymer membrane may be manipulated to take the form of a tube, disc, or diced tape and used in multiphase reaction systems. The supported catalyst particles are composed of at least one finely divided metal catalyst dispersed on a porous support substrate. The catalytic membrane composite may be used in multiphase chemical reactions in a variety of different classes including, but not limited to, hydrogenations, hydrogenolysis, nitro group reductions, hydrodehalogenations, hydrodesulphurization, hydrocracking, hydrodenitration, and deoxygenation. The catalytic membrane composite may be introduced to a stirred tank autoclave reactor system, a continuous flow reactor, or a Parr Shaker Reactor and used to effect the catalytic reaction. In the instant disclosure, the catalytic article is not configured as a contactor (i.e., the porous fibrillated polymer membrane is not used to separate the phases of the reaction.)

The porous supported catalyst particles may be also used in preparation of agrochemical, industrial chemicals, specialty chemicals, flavors, fragrances, food stuffs, fuels, materials for use in organic light emitting diodes, polymers for lithography, active pharmaceutical ingredients, or intermediates to such active pharmaceuticals. In the space of chemicals, the porous supported catalyst particles can be used in the preparation or modification of analgesics, lipids, anti-inflammatories, statins, cholesterol inhibitors, insulin stimulators, treatments for diabetes, treatments for heart disease, pain medications, metabolites, neurotransmitters, agonists, antivirals, opioids, nucleic acids, enzyme inhibitors, antibiotics, polypeptides, oligonucleotides, alkaloids, glycosides, lipids, non-ribosomal peptides, phenazines, natural phenols (including flavonoids), polyketides, color bodies, polymers, terpenes, steroids, tetrapyrroles, adjuvants, polysaccharides, herbicides, pesticides, enzymes, antibodies, and other chemicals with specific commercial applications.

The supported catalyst particles are formed of at least one finely divided catalytic metal that is supported on and/or within a support substrate. As used herein, the term "finely divided" is meant to denote catalytic metals that are present in particles or grains that have an average particle size less than ten microns in diameter. In some embodiments, the finely divided catalytic metal has a range from about 3 μm to about 0.1 nm, from about 3 μm to about 5 nm in diameter, or from about 1 μm to about 1 nm in diameter. Catalytic metals suitable for incorporation onto the support substrate include elements selected from Group Vb, Group VIb, Group VIIb, Group VIIIb, and Group Ib metals of the periodic table. Non-limiting examples of metal catalysts include cobalt, nickel, Raney-type metals or sponge nickel, palladium, platinum, copper, cobalt, rhodium, ruthenium, and rhenium. In some embodiments, mixtures of catalytic metals (e.g., palladium and nickel or copper chromium oxides) are dispersed onto the support substrate.

The finely divided metal catalysts may be dispersed onto and/or into the support substrate by known and optimized processes described in the art including, but not limited to, precipitation, plating, atomic layer deposition, and molecular layer depositions. Incipient wetness from a salt solution of the catalytic metal is one non-limiting example of a method for incorporating a catalytic metal on the substrate particle. The metal catalyst loadings onto the support substrate may range from about 0.1 to about 25% by weight, from about 0.5 to about 15% by weight, or from about 1 to about 10% by weight of the supported catalyst particle. The support substrate may comprise from about 75% to about 99.9%, from about 85% to about 99.5%, or from about 90% to 99% by weight of the supported catalyst particle. High catalytic activity is gained by the effective fine dispersion of the finely divided metal catalyst such that the metal catalyst covers the support substrate and/or is interspersed in the pores of the support substrate.

The support substrate is not particularly limiting so long as it does not affect the multiphase catalytic reaction in which it is used. In exemplary embodiments, the support substrate is porous. Examples of materials for use as the support substrate include, but are not limited to, metals, metal oxides (e.g., aluminum oxide), silica, clays, diatomaceous earth (e.g., kieselguhr), zeolites (e.g., X, Y, A, and ZSM), carbon, and activated carbon. In at least one embodiment, the support substrate is spherical in shape and has a diameter in the range from about 10 μm to about 300 μm, from about 10 µm to about 150 µm, or from about 10 µm to about 30 µm; or from about 0.5 µm to about 10, from about 0.5 µm to 5 µm, from about 0.5 µm to about 4 µm, from about 0.5 µm to about 3 µm, from about 0.5 µm to about 2 µm, or from about 0.5 µm to 1.0 µm. It is to be appreciated that the term support substrate is not meant to be limiting, and particles, flakes, fibers, nanotubes, nanoparticles, platelets, and powders are considered to be within the purview of the present disclosure. FIG. 1 is a scanning electron micrograph (SEM) of an exemplary spherical supported substrate with a finely divided metal on its surface.

As discussed above, the supported catalyst particles are durably enmeshed in an expanded polymer matrix. As used herein, the phrase "durably enmeshed" is meant to describe a supported catalyst particle that is non-covalently immobilized within the fibrillated microstructure of the polymer membrane. No separate binder is present to fix the supported catalyst particles in the membrane. Additionally, the supported catalyst particle is located throughout the thickness of the fibrillated polymer membrane. The porous nature of the fibrillated polymer membrane allows free access to the supported catalyst particles (solid phase) by the liquid/gas mixture (liquid/gas phase). Additionally, the porous fibrillated membrane may have a pore size from about 0.1 µm to about 355 µm (or higher), from about 0.1 µm to about 200 µm, about 0.1 µm to about 100 µm, or from about 0.1 µm to about 40 µm as determined by mercury poroisometry.

The polymer forming the fibrillated polymer membrane is a solvent inert or solvent resistant polymer. In particular, the polymer may be both insoluble and inert to the reactants and products of the multiphase chemical reaction in which it is used. The fibrillated polymer membrane may comprise polytetrafluoroethylene (PTFE), expanded polytetrafluoroethylene (ePTFE), poly(ethylene-co-tetrafluoroethylene) (ETFE), ultrahigh molecular weight polyethylene (UHMWPE), polyethylene, polyparaxylene (PPX), polylactic acid (PLLA), polyethylene (PE), expanded polyethylene (ePE), and any combination or blend thereof. It is to be understood that throughout this disclosure, the term "PTFE" is meant to include not only polytetrafluoroethylene, but also expanded PTFE, modified PTFE, expanded modified PTFE, and expanded copolymers of PTFE, such as, for example, described in U.S. Pat. No. 5,708,044 to Branca, U.S. Pat. No. 6,541,589 to Baillie, U.S. Pat. No. 7,531,611 to Sabol et al., U.S. Pat. No. 8,637,144 to Ford, and U.S. Pat. No. 9,139,669 to Xu et al. The porous fibrillated polymer membrane may also be formed of one or more monomers of tetrafluoroethylene, ethylene, ρ-xylene, and lactic acid. In at least one embodiment, the porous fibrillated polymer membrane is comprised of solvent inert sub-micron fibers of an expanded fluoropolymer.

In some embodiments, the fibrillated polymer membrane is a polytetrafluoroethylene (PTFE) membrane or an expanded polytetrafluoroethylene (ePTFE) membrane having a node and fibril microstructure. The fibrils of the PTFE particles interconnect with other PTFE fibrils and/or to nodes to form a net within and around the supported catalyst particles, effectively immobilizing them. Therefore, in one non-limiting embodiment, the fibrillated polymer membrane may be formed of a network of PTFE fibrils immobilizing and enmeshing the supported catalyst particles within the fibrillated microstructure.

The porous fibrillated polymer membrane may be formed by blending fibrillating polymer particles with the supported catalyst particles in a manner such as is generally taught in United States Publication No. 2005/0057888 to Mitchell, et al., United States Publication No. 2010/0119699 to Zhong, et al., U.S. Pat. No. 5,849,235 to Sassa, et al., U.S. Pat. No. 6,218,000 to Rudolf, et al., or U.S. Pat. No. 4,985,296 to Mortimer, Jr., followed by uniaxial or biaxial expansion. As used herein, the term "fibrillating" refers to the ability of the fibrillating polymer to form a node and fibril microstructure. The mixing may be accomplished, for example, by wet or dry mixing, by dispersion, or by coagulation. Time and temperatures at which the mixing occurs varies with particle size, material used, amount of particles being co-mixed, etc. and are easily identified by those of skill in the art. The uniaxial or biaxial expansion may be in a continuous or batch processes known in those of skill in the art and as generally described in U.S. Pat. No. 3,953,566 to Gore and U.S. Pat. No. 4,478,665 to Hubis.

The porous fibrillated polymer membrane may be utilized in multiphase catalyzed reactions. There are numerous categories of multiphase catalyzed reactions including those with gas plus liquid reactants, gas plus liquid plus a second immiscible liquid phase reactants, liquid plus immiscible/liquid phase reactants, or gas plus condensed liquid vapor phase reactants and various other combinations with at least two distinct phases of matter exist for such reactants that can be used with the porous fibrillated polymer membrane. These reactions may be carried out where the porous fibrillated polymer membrane is located, for example, in a stirred tank autoclave reactor system, a continuous loop reactor, or a Parr Shaker Reactor as described herein. In one non-limiting embodiment, the porous fibrillated polymer membrane may be used in the hydrogenation of a solvated compound in a liquid or a compound in a mixture of immiscible liquids. Non-limiting examples of solvents that may be employed in three-phase reactions include lower alcohols (e.g., methanol and ethanol), tetrahydrofuran, and glycols (e.g., ethylene glycol and diethylene glycol). The solvent may be present in the hydrogenation reaction in an amount from about 1% to about 99%, from about 1% to about 75%, or from about 1% to about 50% by weight of the charge.

Figure 2:
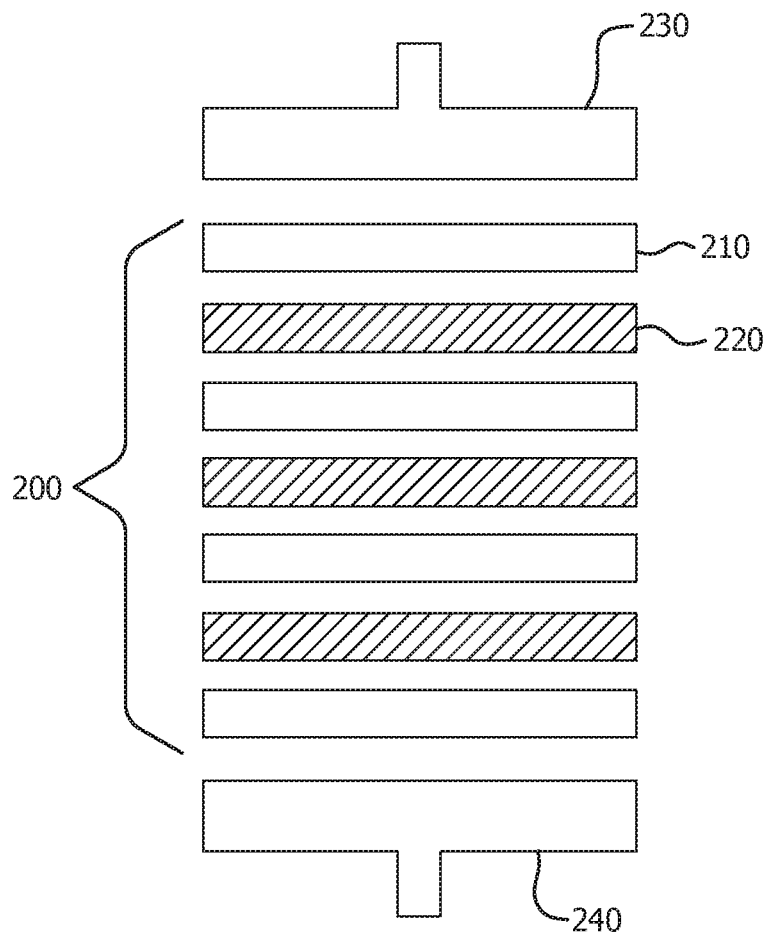
FIG. 2 is an exploded view of a stack of discs interspaced with a spacer material positioned between two metal plates in accordance with at least one embodiment.

In one exemplary embodiment, the porous fibrillated polymer membrane may be cut into immobilized catalyst discs 210 and stacked into disc stack 200 with intervening spacers 220 as shown in FIG. 2 for use in a stirred tank reaction vessel. The intervening spacers 220 may be washers or a scrim or plastic material (e.g., polyvinylidene fluoride (PVDF) scrim) The disc stack 200 may be positioned between a top alignment plate 230 and a bottom alignment plate 240 that are mechanically interconnected, such as by screws or bolts, to securely hold the disc stack 200 together.

Figure 3A:
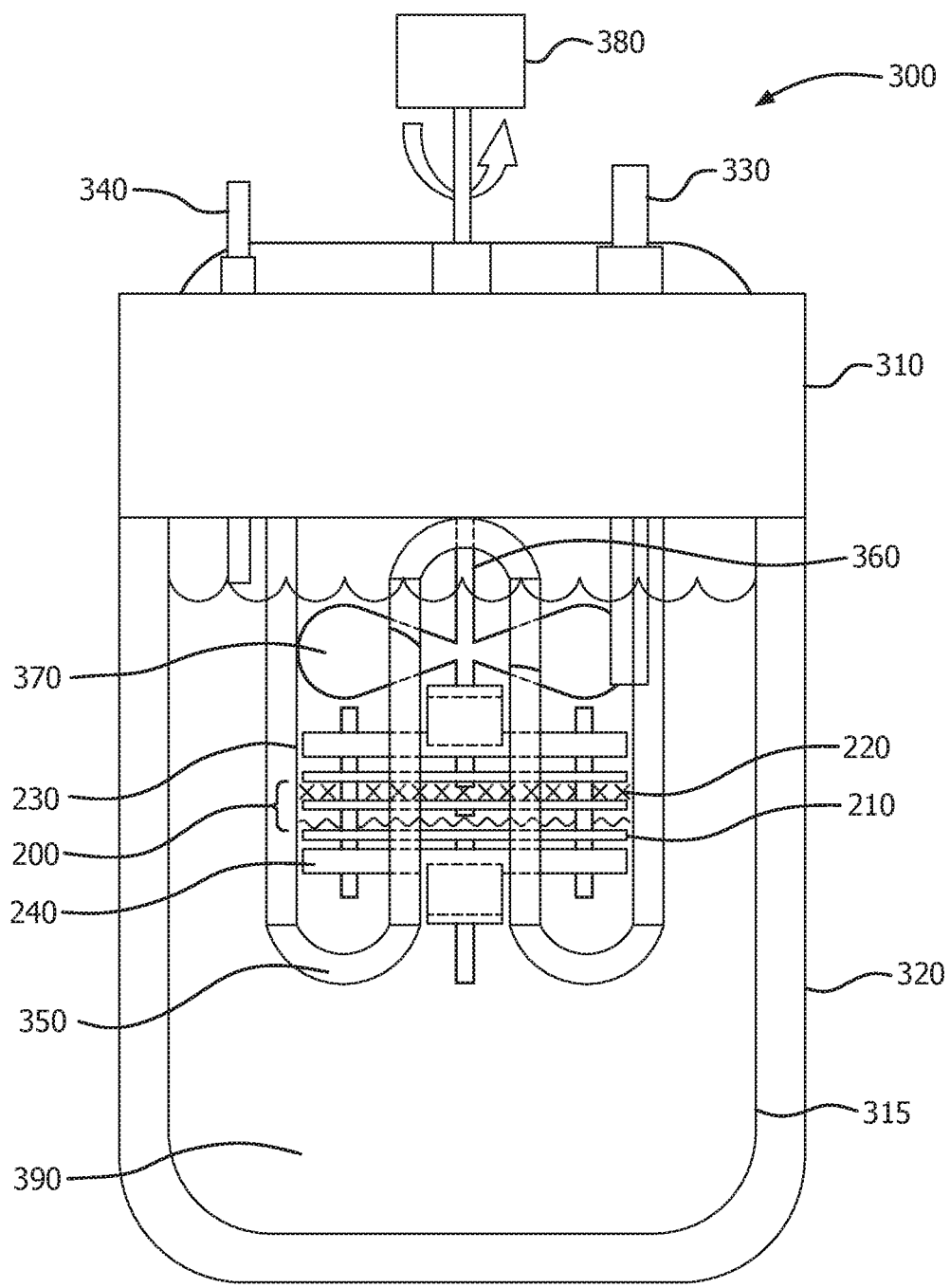
FIG. 3A is a schematic illustration of an autoclave reactor containing a disc stack in accordance with at least one embodiment.

Turning to FIG. 3A, a schematic illustration of an autoclave reactor 300 (e.g. a stirred tank reaction vessel) containing the disc stack 200 may be seen. The autoclave reactor 300 may include a lid 310 removably affixed to an autoclave tank reservoir 315. The tank reservoir is jacketed by a heating mantle 320. The lid 310 includes an inlet 330 for a temperature probe and an inlet 340 to introduce hydrogen gas into the reaction system. A cooling loop 350 may be present in the autoclave tank. The disc stack 200 is mounted on a rotatable impeller shaft 360 having thereon an impeller blade 370 and inserted into the reaction mixture 390. It is to be appreciated that the impeller blade 370 may be positioned on the impeller shaft 360 at any location along the shaft 360 so long as the impeller blade 370 is rotatable within the tank 315 and stirs the reaction mixture 390 through the disc stack 200. In addition, more than one impeller blade may be positioned on the impeller shaft 360, either above, below, or above and below the disc stack 200. The impeller blade 370 depicted in FIG. 3A is not meant to be limiting, and the impeller blade 370 may be formed of one or more blades, spiral structures, or be an impeller turbine.

Figure 3B:
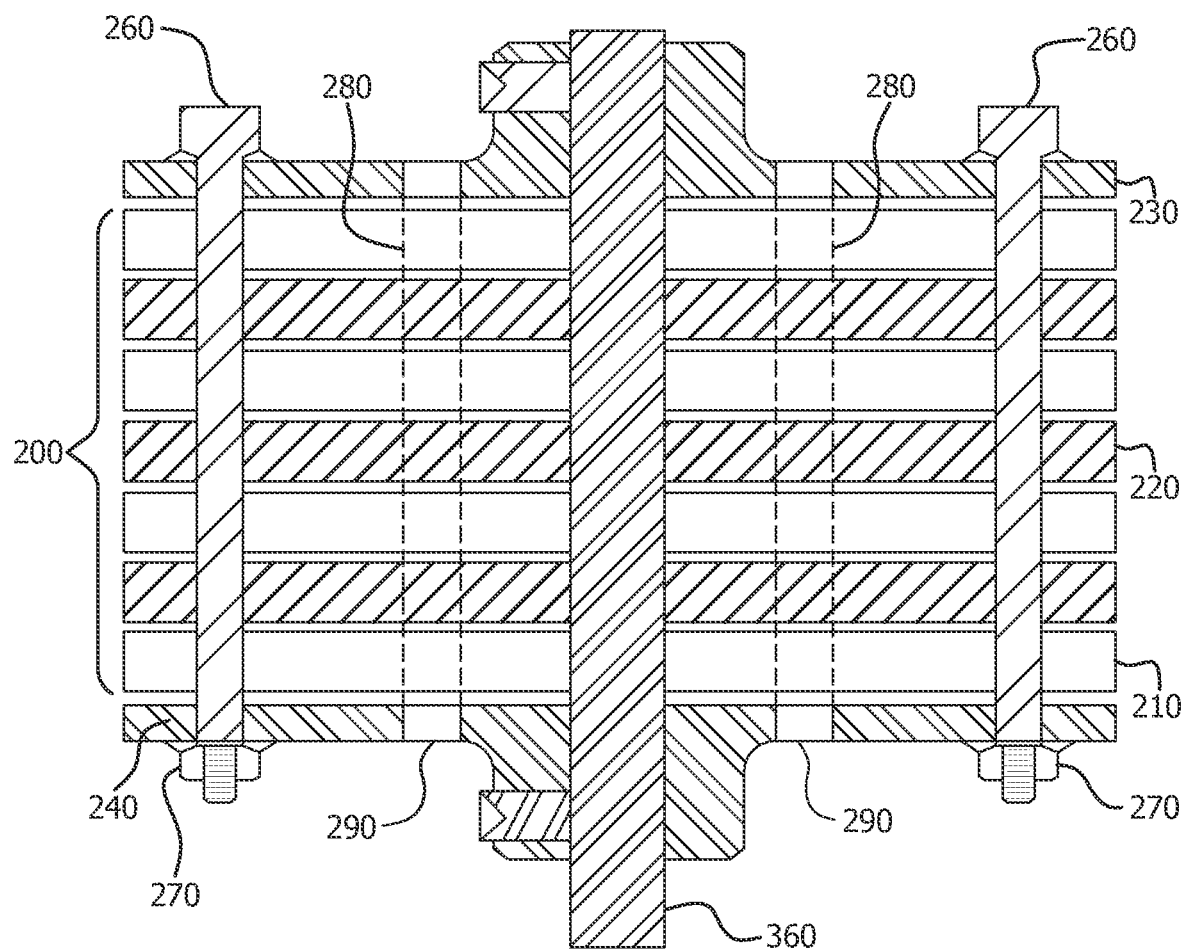
FIG. 3B is a schematic illustration of a stack of discs interspaced with a spacer material positioned on an impeller shaft in accordance with at least one embodiment.

FIG. 3B schematically depicts an enlarged view of the disc stack 200 on the impeller shaft 360. As shown, the impeller shaft 360 extends through the center of the disc stack 200. Through-holes 280 extend through the plane of the catalytic discs 210 and intervening spacers 220 and permit circulation through the disc stack 200. The through-holes 280 also extend through the first alignment plate 230 and the second alignment plate 240. It is to be appreciated that the catalytic discs 210 and intervening spacers 220 may be positioned such that the through-holes 280 in discs 210 and spacers 220 align with each other to form holes 290 through the entire disc stack 200. Any number of through-holes may be located within the catalytic discs 210 and the intervening spacers 220. The alternating stack of immobilized catalyst discs 210 and spacers 220 is positioned between the first alignment plate 230 and the second alignment plate 240, and is held together by bolts 260 and screws 270.

The reaction mixture 390 includes the liquid/gas phase of the three-phase catalytic reaction. The impeller shaft 360 and the impeller blade 370 may be driven by a motor 380. To effect a catalytic reaction, the impeller blade 370 with the attached disc stack 200 are rotated within the autoclave tank 315, effecting a mixing motion within the tank 315. The disc stack 200 containing the immobilized catalyst discs 210 rotate with the shaft 360 such that reaction mixture 390 is recirculated between the discs 210 and through the autoclave tank 315. Due to the porous structure of the fibrillated polymer membrane, the reactant(s) in the reaction mixture 390 are able to move through the immobilized catalyst discs 210 and react with the finely divided catalyst on the supported catalyst particles. Unlike reaction systems that use binders and other polymers, the immobilized catalyst discs 210 do not block the surfaces of the supported catalyst particles, allowing movement of the reactant(s) through and around the discs 210.

Figure 3C:
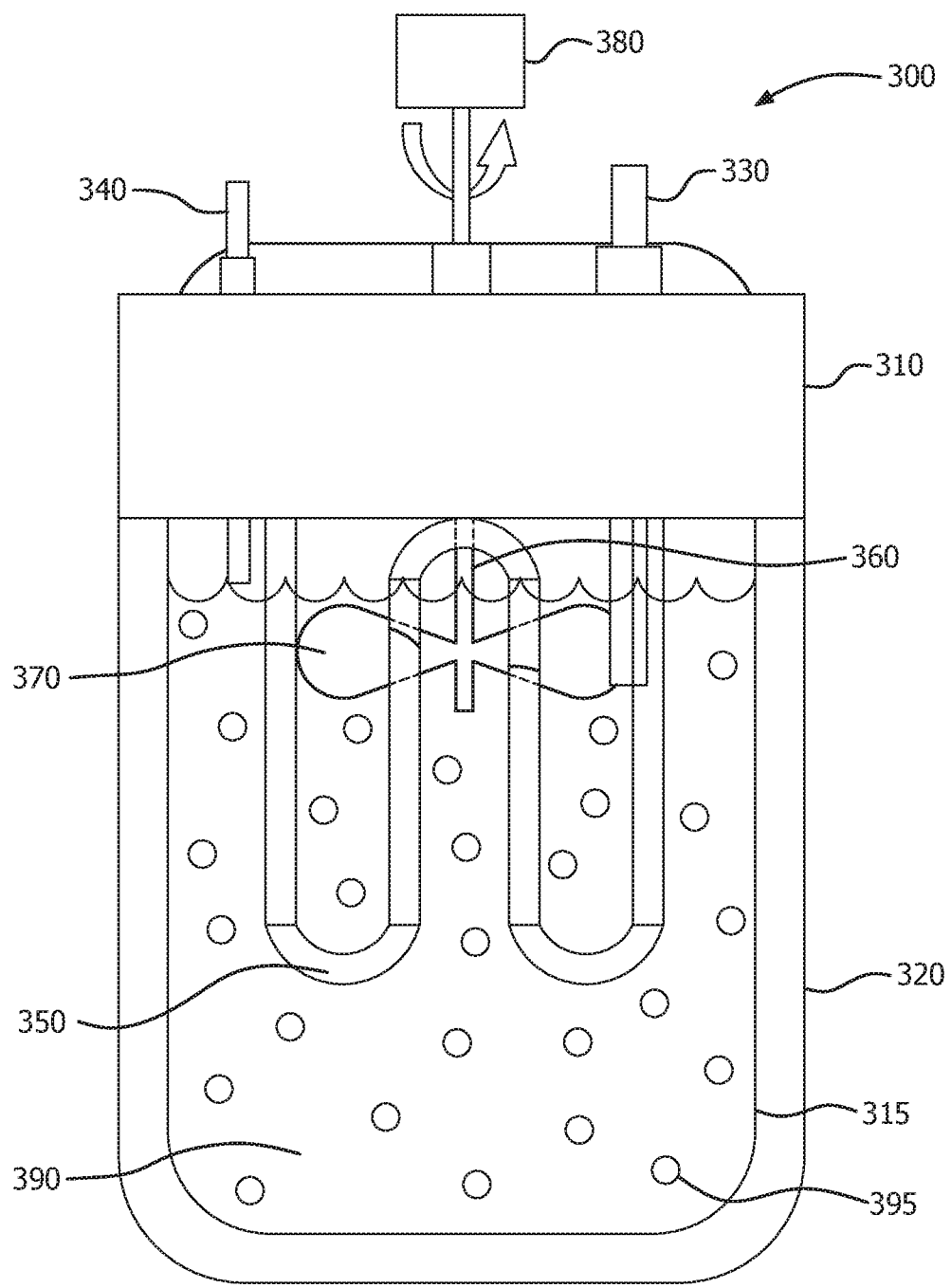
FIG. 3C depicts an encapsulation device containing diced tape therein in accordance with at least one embodiment.

In an alternate embodiment depicted generally in FIG. 3C, the porous fibrillated polymer membrane may be cut or diced, such as into a geometric shape (e.g. a square, rectangle, circle, triangle, etc.) which is referred to herein as "diced tape". To effect a catalytic reaction, the impeller blade 370 effects a mixing motion within the tank 315, thereby causing the diced tape 395 to move within the reaction mixture 390. Due to the porous structure of the fibrillated polymer membrane, the reactant(s) in the reaction mixture 390 are able to move through and around the diced tape 395 and react with the finely divided catalyst on the supported catalyst particles.

Figure 4:
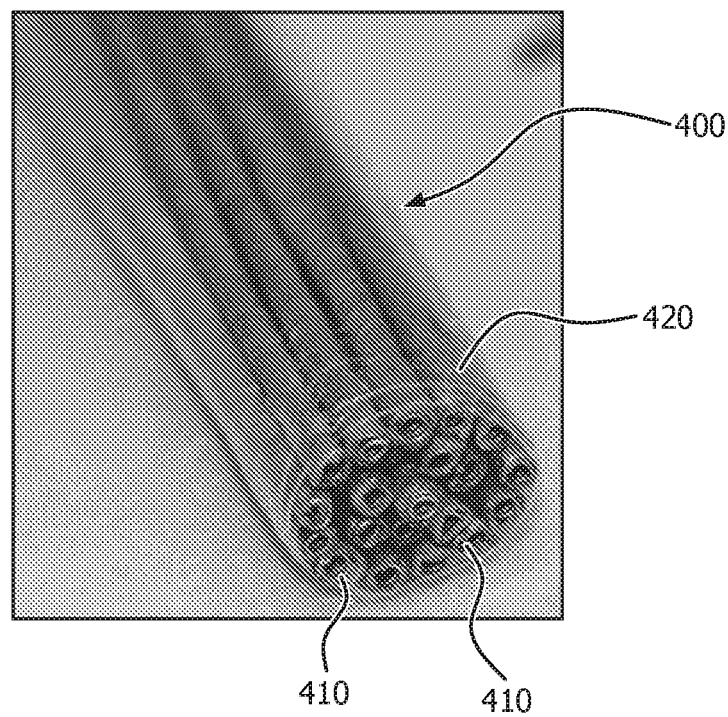
FIG. 4 is an image depicting tubes formed from a porous fibrillated polymer membrane in a tubular array in accordance with at least one embodiment.

In another embodiment, the porous fibrillated polymer membrane may be slit or cut into strips and wound around a tubular support member at a desired pitch, e.g. from about 40° to about 60°. Non-limiting examples of suitable tubular support members include stainless steel springs, braided wire, extruded porous polymeric tubes, perforated metal tubes, and plastic or metal static mixers. Depending on the desired length and the length of the wrapped tubular support member, the wrapped tubular support member may be cut to the desired length to form tubes. As shown schematically in FIG. 4, the tubes 410 may be bundled together into a tubular array 400 for insertion into a reactor. In one embodiment, the tubes 410 are bundled together with a plastic film 420.

Figure 5A:
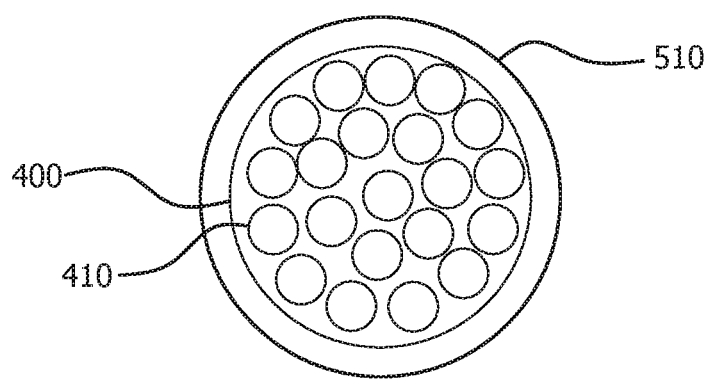
FIG. 5A is a schematic illustration of a top view of the tubes immobilized in a reactor in accordance with least one embodiment.
Figure 5B:
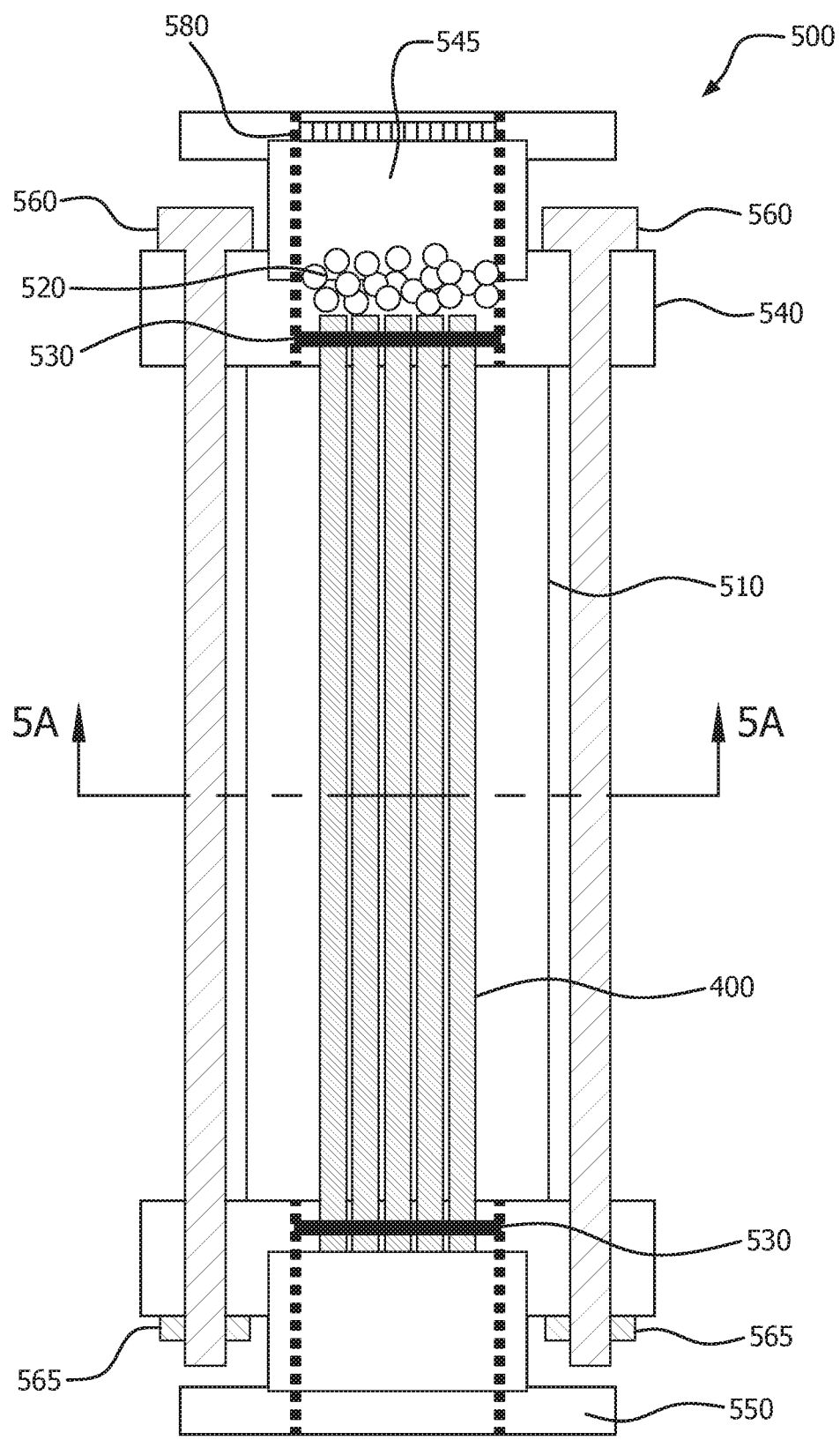
FIG. 5B is a schematic illustration of a reaction system including the reactor shown in FIG. 5A in accordance with least one embodiment.

Turning to FIGS. 5A and 5B, these tubes 410 (or the wrapped tubular support members) may be installed into a reactor assembly 500 such that they are immobilized. As shown in FIG. 5B, the tubular array 400 may be inserted into a glass tube 510 (e.g., sight glass tube) and sealed at each end thereof with sanitary gaskets 530. The gaskets 530 may be formed of rubber, such as Viton™ sanitary gaskets. The glass tube 510 containing the tubular array 400 may be mounted between an upstream sanitary connector 540 and a downstream sanitary connector 550. The sanitary connectors 540, 550 may be held together by bolts 560 and nuts 565. A perforated plate 580 may be placed in the upstream sanitary connector 540 and the tube 545 of the upstream sanitary connector 540 may be filled with glass beads 570 for flow distribution.

To effect a catalytic reaction, the reactor assembly 500 may be fluidly connected to a container containing a reaction mix containing the liquid/gas phase. The reaction mixture may be pumped or otherwise fed into the reaction assembly 500 through the perforated plate 580 and glass beads 570. Both the perforated plate 580 and the glass beads 570 distribute the flow of the reaction mixture so that it is evenly or substantially evenly distributed through the tubes 410. The reaction mixture is passed through the tubes 410 located in the reactor assembly 500, where the liquid/gas phase in the reaction mixture is contacted with the supported catalyst particles (solid phase) enmeshed in the porous fibrillated polymer membrane forming the tubes 410. In one embodiment, the reactor assembly 500 may be inserted into a continuous flow reaction system, such as the continuous flow reaction system 600 depicted generally in FIG. 6 and discussed in detail in the section below entitled "Continuous Loop Reactions in a Packed Tubular Array". Due to the porous structure of the fibrillated polymer membrane, the reactant(s) in the reaction mixture are freely able to move through the tubes 410 in the reactor assembly 500 and react with the finely divided catalyst on the surface of the supported catalyst particles. In addition, the distribution of the supported catalyst particles within the porous fibrillated polymer membranes allow for uniform catalyst activity and distribution over the length of the tubes 410. Additionally, the reaction mixture may flow through the interstitial spaces between the tubes 410 and not only through the lumen of the tubes 410. In addition, the reactor assembly 500 demonstrates an advantageously lower pressure drop in comparison to conventional packed beds of powder or pellets.

Figure 7:
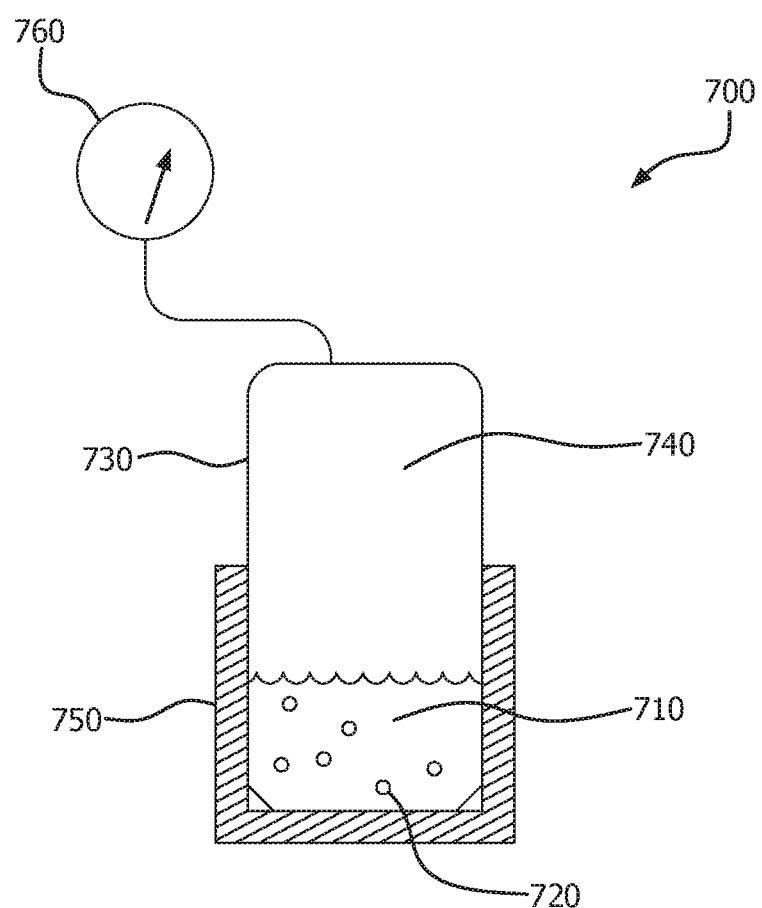
FIG. 7 is a schematic illustration of a Parr Shaker Reactor using diced tape containing supported catalyst particles in accordance with at least one embodiment.

In yet another embodiment, a porous fibrillated polymer membrane may be cut or diced, such as into a geometric shape (e.g. a square or rectangle) which is referred to herein as "diced tape". The diced tape may be utilized in a Parr Shaker Reactor, such as is schematically depicted in FIG. 7. As shown, a reaction mixture 710 containing the liquid/gas phase of the three-phase catalytic reaction is placed into a tank 730 together with the diced tape 720 containing the supported metal catalysts. The tank 730 is then pressurized with a gas 740 (e.g., hydrogen). A pressure gauge 760 may be used to monitor the internal pressure of the tank 730. A heating jacket 750 provides heat to the tank 730 for the reaction process. To affect a catalytic reaction, the tank 730 is shaken by a shaking device (not illustrated), thereby creating a mixing motion within the tank 730. As a result, the diced tape 720 is circulated within the reaction mixture 710. Due to the porous structure of the fibrillated polymer membrane, the reactant(s) in the reaction mixture 710 have free access to move through and around the diced tape 720 and react with the finely divided catalyst on the surface of the supported catalyst particles.

Figure 11:
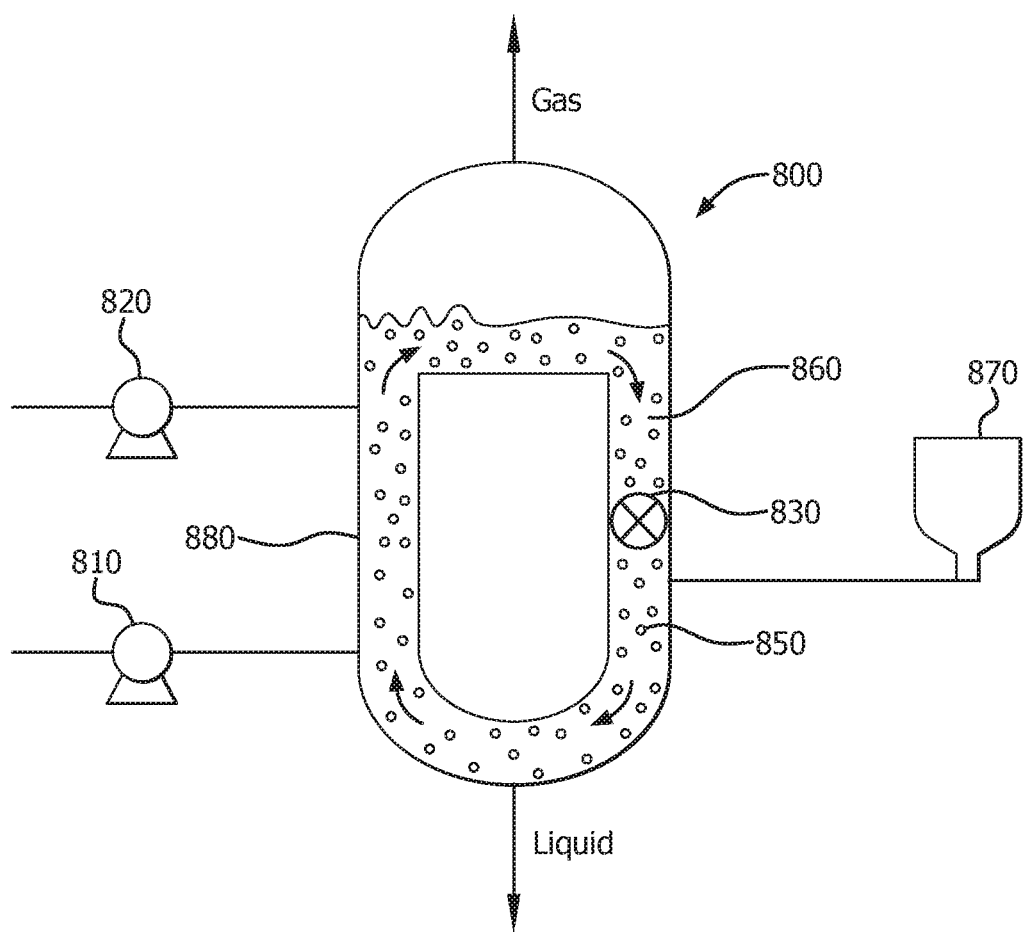
FIG. 11 is a schematic illustration of a continuous loop reactor using diced tape in accordance with least one embodiment.

In a further embodiment, the porous fibrillated polymer membrane in the form of diced tape may be used in a continuous loop reactor such as is illustrated in FIG. 11. The continuous loop reactor 800 includes a gas metering pump

810, a liquid metering pump 820, a diced tape metering member 870, and a pump 830 to circulate the reaction mixture 860 around the looped reactor 800. The gas reactant(s) and liquid reactant(s) are fed into the reactor tank 880 via the gas and liquid metering pumps 810, 820, respectively, to form the reaction mixture 860. The diced tape 850 is introduced into the reaction mixture 860 via the diced tape metering member 870. To effect a catalytic reaction, the pump 830 effects a circular motion of the reaction mixture 860 within the tank 880, thereby causing the diced tape 850 to move within the reaction mixture 860. Due to the porous structure of the fibrillated polymer membrane, the reactant(s) in the reaction mixture 860 are able to move through and around the diced tape 859 and react with the finely divided catalyst on the supported catalyst particles.

In the embodiments described above, the porous fibrillated polymer membrane effectively distributes the supported metal catalysts throughout the membrane, in both the length and thickness directions. In addition, the porous nature of the fibrillated polymer membrane allows for efficient and reliable transport of multiphase reactants and products to and from the catalyst surface. Further, catalyst loss is minimized as a result of the supported catalyst particles being durably enmeshed within the fibrils of the porous fibrillated polymer membrane.

Test Methods

It should be understood that although certain methods and equipment are described below, other methods or equipment determined suitable by one of ordinary skill in the art may be alternatively utilized.

Formation of Disc Stack

Porous fibrillated polymer membranes described in the Examples were die cut into discs with 9 holes: 8 holes with ⅝ inch diameter and one center hole for the shaft having a 0.380 inch diameter. These immobilized catalyst discs were then assembled into a disc stack using bolts in the outer four holes for mounting onto stainless steel alignment plates Discs were stacked and spaced apart by washers and similarly die cut disks of a polyvinylidene fluoride (PVDF) expanded plastic mesh (Dexmet Corporation, Wallingford, Conn.). The PVDF mesh spacers had a thickness of 0.020" (~0.051 cm), a strand width of 0.010" (~0.025 cm), and diamond shaped openings with a (LWD) long width dimension of 0.158" (~0.401 cm) and a short width dimension (SWD) of 0.125" (~0.318 cm). The immobilized catalyst discs and PVDF mesh spacers were stacked using washers with a spacing of 0.125" (~0.318 cm) between discs and the PVDF mesh spacers. A separation of 0.125" (~0.318 cm) was also kept between the top and bottom discs and the respective stainless steel alignment plate. The disc stack and stainless steel alignment plates were bolted together using screws and nuts. A set screw was then used to secure the disc stack to the impeller shaft in the reactor apparatus (e.g., autoclave reactor or stirred reactor) such that the disc stack would turn with the impeller shaft of the reactor apparatus. Thus the immobilized catalyst discs would rotate with the impeller shaft such that reaction mixture (e.g., liquid/gas phase) would be recirculated between the discs and through the tank of the reactor.

Parr Shaker Reaction and Reactor Description

A Model 3910 Parr hydrogenation apparatus (Parr Instrument Company, Illinois), also known as a "Parr shaker" was used. Reactions were carried out in neoprene stoppered 500-mL Parr glass bottles. The bottles were jacketed with a heating mantle and metal guard commercially available from Parr Instrument Company. To conduct the reaction, the glass bottles were charged with either 100 mL of the EAQ working solution or 100 mL of s-limonene 96% purity from Sigma Aldrich. Catalyst was then added in the amount noted in the Example. The bottle was capped and mounted in the Parr shaker with the neoprene stopper through which a gas inlet line and thermocouple immersed in the solvent were added. The bottle was then purged of air by pressurization with hydrogen to 50 psi (~0.35 MPa) and vented repeatedly.

After purge, the bottle was pressurized to 5 psi (~0.035 MPa) with hydrogen, the Parr shaker was started, and the temperature control set point was turned on and set to 50° C. (EAQ working solution) or 25° C. (limonene). After coming up to temperature (5-10 minutes), the shaking was stopped, the bottle was pressurized to 50 psi (~0.35 MPa), and the pressure reservoir valve was closed so that the system included the bottle and gas line to the pressure gauge with approximately 420 mL of hydrogen head space. The shaker was then started at 4 hertz (Hz) frequency and the pressure inside the bottle recorded and monitored for 10 minutes as described in the respective example. Hydrogenation reaction progress was then assessed based on pressure decrease in the reactor.

Stirred Tank Autoclave Reactions and Apparatus

For tests using conventional supported catalyst slurry powder and disc stacks with supported catalyst particles immobilized in porous fibrillated membranes, the same 1 gallon (~3.79 Liters) autoclave tank was used. The reactor was an Autoclave Engineers 1 gallon (~3.79 Liters) HASTELLOY® C (a corrosion resistant alloy composed of nickel, molybdenum, chromium, and iron) vessel, model number N6657HC, rated at 2200 psi (~15.17 MPa). The vessel uses a magnetic coupling to the central drive shaft for a bearing attached impeller inside the reactor. The magnetic coupler is attached to an external electric motor or an air motor via a belt drive as noted in the Example. The stir speed was set at 300 revolutions per minute (rpm) or 350 rpm as noted in the Example.

For all experiments, the reactor was charged with 1 L of EAQ working solution prepared as described below. Catalyst was added in the amount noted in the Example, and the reactor was purged to remove air using sequential pressurization/depressurization while stirring with hydrogen at room temperature. The reactor was equipped with an electric heating jacket monitored by a thermocouple through a thermowell in the vessel lid and controlled via a proportional integral derivative (PID) tuned electronic temperature controller. The temperature control was set to the noted temperature set forth in the Example. The reactor was equilibrated with charge at this temperature for one hour within +/-2° C. at 50 psi (~0.35 MPa) of hydrogen without stirring prior to starting the reaction unless otherwise noted. At the start of the reaction, the temperature controller for the heating element was turned off. Pressure in the reactor was monitored directly from a digital pressure gauge mounted in the reactor lid.

To initiate a reaction run, the reactor was sealed and pressurized to the noted set pressure with hydrogen, for example, 50 psi (~0.35 MPa) or 200 psi (~1.38 MPa), respectively. Stirring was initiated, and the temperature controller for heating was turned off. The pressure was recorded at set intervals for the duration of the reaction as noted in the Examples.

Hydrogenation reaction progress was then assessed based on pressure decrease in the reactor. The reactor was equipped with a tubular water cooling loop (though it was not used for cooling) and was filled with hydrogen during the experimental runs. No baffles were inserted for these experiments, though the immersed water cooling loop provided some baffling in the experiments conducted. The action of the turbine impeller created a low pressure zone at the point of agitation. That rotation of the turbine causes the hydrogen to break into finely divided bubbles and cause dissolution of hydrogen in the respective liquid working solution. In doing so, a frothy mixture was created which was helpful in bringing both reactant phases to the catalyst surface. In addition, the rotating action of the impeller lead to uniform suspension of powdered catalyst throughout the liquid in examples where the structured catalyst particle was present in a free form.

After each test and between runs, the reactor was depressurized, the working solution removed via draining, the reactor was subjected to multiple rinse and drain steps using a volatile co-solvent for the EAQ working solution until all surfaces were visibly clean and free from catalyst particles. The reactor was then dried and charged for the next reaction as described in the Examples. For sequential experiments using the same catalyst charge, the catalyst was vacuum filtered from the working solution on Whatman number 2 filter paper (Thermo Fisher Scientific) to recover the powdered catalyst. The catalyst was then carefully scraped off the filter paper with care to avoid damaging the filter, and put back into the reactor for the next charge.

Continuous Loop Reactions in a Packed Tubular Array

To further demonstrate the breadth of the instant invention of a powdered catalyst comprising metal dispersed on a porous support particle where the support particle is immobilized in a fibrillary porous matrix for multiphase chemical reactions beyond batch conditions, the following experimental apparatus for continuous flow reactions was used.

A porous fibrillated polymer membrane having a porosity from about 30% to about 95% was slit to a width of 0.25 inches (~0.64 cm) and spiral wrapped at a 52° angle onto a stainless steel stock spring (McMaster-Carr, Robbinsville, N.J., item #9663K64—W.B. Jones part #732; W.B. Jones Spring Company, Wilder, Ky.) previously stretched to ~150% of its original length and heat set at total length of 15 inches (~38.1 cm) and nominal outer diameter of 0.096 inches (~0.244 cm). The tubular wrapped spring was tacked in place with a molten plastic film at 5 inch (~12.7 cm) intervals and cut into 5 inch (~12.7 cm) tubes. Each wrapped tube had (~5 g/21 tubes or ~0.24 g) grams of membrane.

Twenty one (21) of the tubes were bundled and wrapped tightly together with a plastic film and mounted in a Viton™ sealed sanitary sight glass with a 6 inch (~15.2 cm) viewable area. The sight glass was mounted into a continuous flow through reactor using Viton™ sanitary gaskets using its 1 inch (~2.54 cm) sanitary flange connectors. A sanitary gasket with perforations was placed in the upstream sanitary connector and the tube of the entrance sanitary flange of the sight glass ahead of the tubular array was filled with glass beads for flow distribution.

Figure 6:
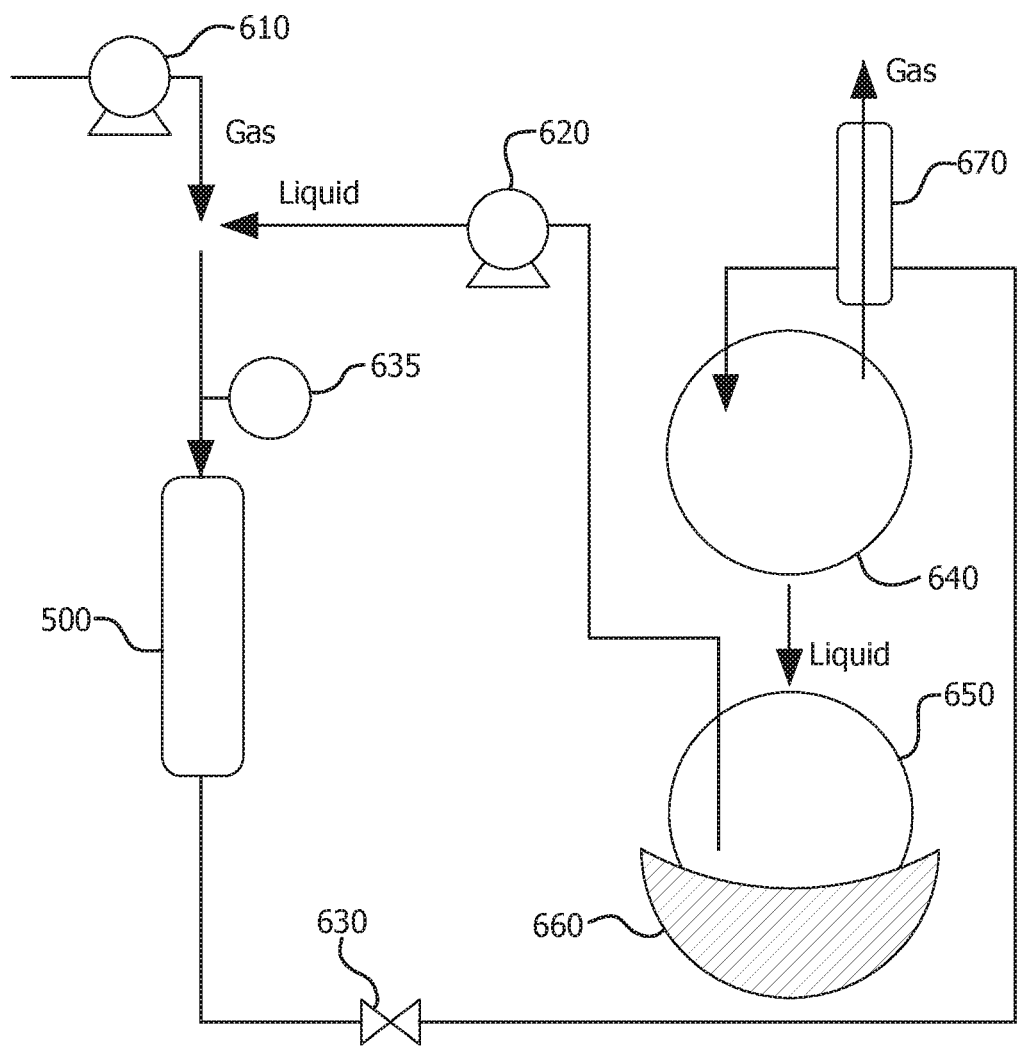
FIG. 6 is a schematic illustration of a continuous loop reactor utilizing a tubular array in accordance with least one embodiment.

The above-described continuous flow through reactor was mounted in the circuit schematically depicted in FIG. 6. The continuous flow through reactor included gas and liquid metering pumps 610, 620, a back pressure valve 630, a pressure gauge 635, a 5-liter gas separator flask 640, a liquid sump 650 comprising a 5-liter 3-neck glass round bottom flask with a thermocouple and PID controlled heating mantle 660 and magnetic stirrer (not illustrated). The separator flask 640 was vented to atmosphere with a glass condenser 670 to prevent evaporation and allow excess hydrogen to escape into the atmosphere. All circuit plumbing was done with ⅜" (~9.5 mm) fluorinated ethylene propylene (FEP) tubing and stainless steel compression fittings.

To prepare the system, the sump round bottom flask 650 was charged with 1.75 L of EAQ working solution and the system was purged with nitrogen. Liquid flow was commenced using the liquid metering pump 620 at 300 mL/min. The heating mantle 660 was set to 50° C. and the system temperature was equilibrated over an hour. To commence reaction, the liquid metering pump 620 was increased to 600 mL/min and the hydrogen gas metering pump 610 was started at 2100 mL per minute, resulting in alternating liquid and gas bubbles being visible in the primary FEP tubing and in spaces between outer tubes in the bundled tube reactor 500 itself. The back pressure valve 630 was adjusted to provide for a hydrostatic pressure in the reactor ahead of the valve set to 36 psi (~0.25 MPa). The differential pressure across the reactor was less than 0.2 psi (~1.38 kPa).

Reaction was commenced via recirculation and 20 mL samples of working fluid were withdrawn through a 0.7 µm fiberglass syringe filter after the reactor at 15 minute intervals. These samples were then oxidized via bubbling with gentle air flow for 20 minutes. A 5-mL aliquot of each sample was then shaken with distilled water for 5 minutes to extract the hydrogen peroxide to the water phase. Each water sample was then titrated using standardized permanganate solutions to quantify the concentration of $H_2O_2$.

Mercury Porosimetry Testing

Porosity measurements were carried out on a Micromeritics AutoPore V mercury porosimeter (Micromeritics, Norcross, Ga., USA), using Micromeritics MicroActive software version 2.0. Quadruple Distilled Virgin Mercury—99.9995% purity (Bethlehem Apparatus, Bethlehem, Pa.) was used as received for tests. Tests used a solid type penetrometer with a bulb volume of 5 cc and a stem volume of 0.392 cc (SN: 07-0979). Pieces of the composite samples were cut into 1 cm×2 cm strips and enough of these strips were weighed on an analytical balance to provide a total mass of approximately 0.25 g. After noting the mass, the sample pieces were placed in the penetrometer.

The test parameters were as follows: (1) the penetrometer was placed into the low pressure port on the AutoPore and evacuated to 50 µm Hg, followed by 5 min unrestricted evacuation; (2) the penetrometer was then filled with mercury at 0.5 psia (~3.5 kPa) and equilibrated for 10 seconds; pressure was subsequently applied to the capillary using nitrogen in steps up to 30 psia (~0.21 MPa), equilibrating for 10 seconds at each step prior to determining the intrusion volume via the standard capacitance measurement with the penetrometer capillary; (3) the penetrometer was removed from the low pressure port after returning to atmospheric pressure and then weighed to determine the amount of mercury added; (4) the penetrometer was subsequently placed into the high pressure port on the AutoPore and the pressure was again increased in a series of steps up to approximately 60,000 psia (~413.7 MPa) allowing 10 sec at each step to equilibrate prior to intrusion volume measurements.

The intrusion volume V at any pressure is determined through a capacitance measurement using the pre-calibrated capillary (i.e., a cylindrical capacitor where the outer contact is the metallized coating on the external surface of the glass capillary, the inner contact is the liquid mercury, and the dielectric is the glass capillary). The total intrusion volume divided by the sample mass gives the specific intrusion volume (in mL/g).

The volume occupied by the sample was calculated at the two extreme target pressures, namely, 0.5 psia (~3.5 kPa)

and 60,000 psia (~413.7 MPa). Since the penetrometer has a known calibrated volume, the difference between this volume and the mercury volume (determined from the mass increase after mercury addition at low pressure and the density of mercury) yields the volume of the sample including any pores. Dividing the mass of the sample by the volume at this low pressure provides the bulk density of the sample. At high pressure, where mercury has been pushed into the pores by an amount given by the intrusion volume, the skeletal density can be approximated by dividing the sample mass by the adjusted sample volume (e.g., low pressure volume minus total intrusion volume).

Total Pore Area

The total pore area reported was determined through a series of intermediate calculations. First, the diameter of the pores being filled at a given pressure was calculated using the Washburn equation:

$$D_i = \frac{-4\gamma \cos\theta}{P_i}$$

where $D_i$=pore diameter at the $i^{th}$ pressure point, $\gamma$=surface tension, $\theta$=contact angle and $P_i$=pressure. The mean diameter for the $i^{th}$ point is then taken to be:

$$Dm_i=(D_i+D_{i-1})/2$$

The incremental specific intrusion volume for the $i^{th}$ point was calculated from the total intrusion volume taken at each point ($I_i$):

$$Ii_i=I_i-I_{i-1}$$

Finally, the incremental specific pore area for the $i^{th}$ point was calculated from the incremental intrusion volume and the mean diameter from:

$$A_i=(4\times Ii_i)/Dm_i$$

The total (i.e., cumulative) specific pore area for the $i^{th}$ point was then calculated as:

$$A_i=Ai_i+Ai_{i-1}+\ldots+Ai_j.$$

Bulk Density

The bulk density of the sample is the density of the solid including all open pores and internal void volume. The bulk density was calculated by dividing the sample mass by the low pressure mercury intrusion volume. Sample mass was determined by weighing on an analytical balance of +/−0.01 mg sensitivity.

$$\text{Bulk Density}=M/(V_{Low\ Pressure})$$

Skeletal Density

The skeletal density is the density of a solid calculated by excluding all open pores and internal void volume. The skeletal density was calculated by dividing the sample mass by the adjusted sample volume (low pressure volume minus total intrusion volume). The sample mass was determined by weighing on an analytical balance of +/−0.01 mg sensitivity.

$$\text{Skeletal Density}=M/((V_{Low\ Pressure})-(V_{High\ Pressure}))$$

where $V_{Low\ Pressure}$ is volume of the sample at 0.5 psia (~3.5 kPa) and $V_{high}$ Pressure is total intrusion volume at 60,000 psia (~413.7 MPa).

Total Porosity

The total porosity within the substrate is simply the void volume of the sample divided by the total volume of the sample. This can be calculated as:

% Porosity=100*(total intrusion volume at 60,000 psia (~413.7 MPa))/(volume of the sample at 0.5 psia (~3.5 kPa)).

Thickness

Membrane thickness was measured by placing the membrane between the two plates of a Kafer FZ1000/30 thickness snap gauge (Kafer Messuhrenfabrik GmbH, Villingen-Schwenningen, Germany). The average of the three measurements was used.

Test Materials

Ethyl Anthraquinone (EAQ) Working Solution

The EAQ working solution was prepared by dissolution of 100 g EAQ in a solution of 666 mL trimethyl benzene (TMB) and 333 mL of trioctyl phosphate (TOP). Both the EAQ and TMB were acquired from Sigma-Aldrich (St. Louis, Mo.). The TOP was acquired from TCI Chemical (TCI America, Portland, Oreg.). All three chemicals were reagent grade (>98% purity) and were used as received without further purification. The EAQ was dissolved into the TMB/TOP solution slowly in a 6-L master batch with gentle heat supplied via a heating mantle controlled to 40° C. with stirring in a closed glass round bottom flask. The starting EAQ working solution was a yellow color.

Separate analytical studies were performed using standard permanganate peroxide titrations to establish that the consumed hydrogen is directly proportional to production of hydrogenated $EAQH_2$ on a molar basis for the Pd/SiAl catalyst employed in the Examples. The consumption of hydrogen is directly proportional to the change in $H_2$ hydrogen gas pressure. Since the molar consumption of hydrogen is directly proportional to the product produced it serves as a direct proxy for the moles of product in calculation of reactivity and productivity metrics.

Limonene Solution 40.8 g of (−)-limonene (Acros Organics, Thermo Fisher Scientific, 96%, CAS 5989-54-8) was dissolved in a total volume of 1000 mL made up of absolute ethanol. This solution was used as made for subsequent reactions without further purification. The reaction of limonene with hydrogen proceeds with quantitative yield. Therefore the consumption of hydrogen is a direct proxy for the molar quantity of methane produced.

EXAMPLES

Unless defined otherwise herein, all technical and scientific terms used herein have the same meaning as commonly understood by one of ordinary skill in the art to which this invention belongs. The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Comparative Example 1

0.225 grams of 2 wt % Pd (0.0045 g Pd metal) on a $SiO_2$—$Al_2O_3$ support—Type 429 powdered catalyst from Johnson Matthey (Royston, United Kingdom) and 100 mL of EAQ working solution were charged to a 0.5-L Parr glass bottle. Prior to reaction the catalyst was preconditioned to ensure any oxidized Pd would be returned to a reduced state by conditioning in the working solution for 1 hour at 55° C. with 50 psi (~0.35 MPa) of constant hydrogen pressure. After preconditioning the catalyst separated from the working solution by decanting, and the reactor was recharged with a fresh 100 mL of EAQ working solution. A hydrogenation reaction was effected at 50° C. as described the section above titled "Stirred Tank Autoclave Reactions and Apparatus".

Hydrogenation of EAQ was successful as evidenced by the working solution color change from yellow to brown and consumption of hydrogen indicated by a pressure change in the bottle of 18 psi (~0.12 MPa) following 10 minutes of agitated shaking of the catalyst powder at 50° C. The final EAQ conversion to $EAQH_2$ was 43.7%. The final productivity at termination of reaction was 437 (based on $H_2$ moles consumed/moles Pd metal).

Comparative Example 2

12.5 grams of 2 wt % Pd by weight on a $SiO_2$—$Al_2O_3$ support—Type 429 powdered catalyst from Johnson Matthey and 1250 mL of EAQ working solution were charged to an Autoclave Engineers 1 gallon (~3.79 L) HASTELLOY® C vessel, model number N6657HC. A hydrogenation reaction was effected as described the section above titled "Stirred Tank Autoclave Reactions and Apparatus" using the standard pitched blade turbine with a metal disc stack and screens, but not including any immobilized catalyst discs described above. Hydrogenation of EAQ was accomplished as evidenced by the working solution color change from yellow to brown at the end of the test and consumption of hydrogen indicated by a pressure change of 73.2 psi (~0.505 MPa) in the reactor monitored over 1 hour.

Following the test, the test fluid containing the slurried powder catalyst was gravity filtered through a 0.7 μm micron pore rated glass fiber filter capsule (Sterlitech Corporation, Kent, Wash.). To accomplish this test a 50-mL polyethylene luer syringe barrel without plunger (Terumo Medical Corporation, Somerset, N.J.) was attached to the capsule and 30 mL of the catalyst slurried in the post reaction working solution was added to the barrel. Effluent from the filter capsule was collected in a 20-mL glass class a graduated cylinder. Volume was noted at time intervals measured by a stop watch.

Figure 8:
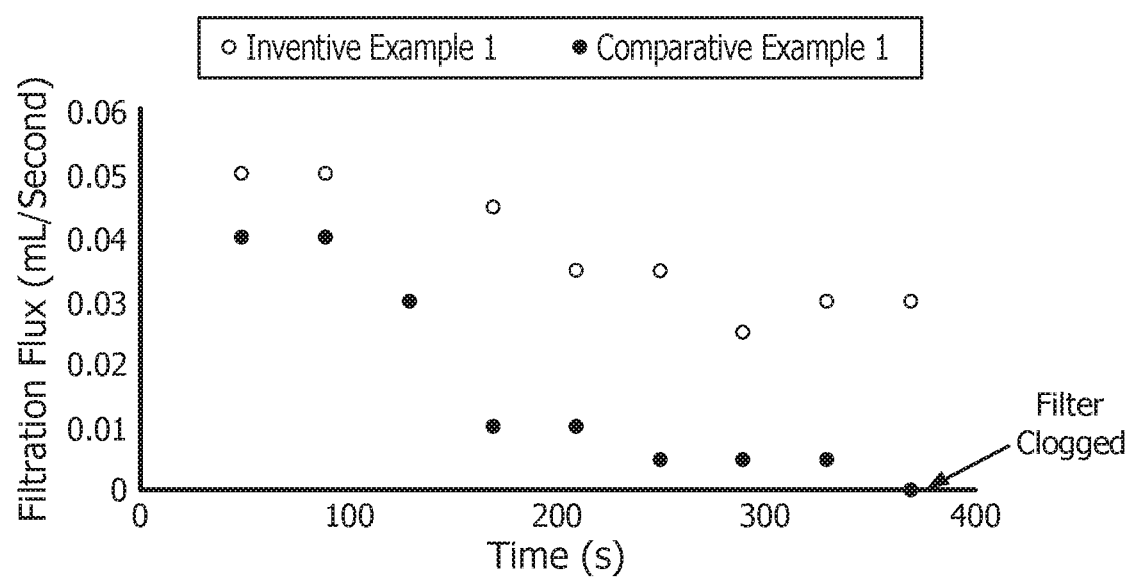
FIG. 8 is a graphical illustration of catalyst removal filtration after multiphase hydrogenation in a stirred autoclave reactor in accordance with at least one embodiment.

Results of this test are recorded plotted in terms of flow/area per unit time or filtration flux in FIG. 8. These results show clearly that the working solution and slurry particles rapidly clog the filter resulting in a decay to zero flux. In addition, and as shown in FIG. 8, the use of the porous fibrillated polymer membranes to enmesh and immobilize the structured catalyst particles resulted no filter clogging (Inventive Example 1) whereas the non-immobilized structured catalyst particles clogged the filter (Comparative Example 1). Thus, ease of processing is vastly improved with the use of the expanded polymer matrices as there is no need to change filters or to remove catalyst particles from the filter. The final EAQ conversion to $EAQH_2$ was 81.1%. The productivity was not calculated since the catalyst was not first preconditioned to ensure starting in a reduced state.

Comparative Example 3

Approximately 2.5 grams of 2 wt % Pd by weight on a $SiO_2$—$Al_2O_3$ support—Type 429 powdered catalyst from Johnson Matthey (Royston, United Kingdom) and 1000 mL of EAQ working solution were charged to a Autoclave Engineers 1 gallon (~3.79 L) HASTELLOY® C vessel, model number N6657HC. A hydrogenation reaction was effected as described the section above titled "Stirred Tank Autoclave Reactions and Apparatus" using the standard pitched blade turbine with a metal disc stack and screens, but not including any immobilized catalyst discs described above. For this the reactor was brought to 55° C., pressurized to 200 psi (~1.38 MPa) with hydrogen, and stirring was initiated. Hydrogenation of EAQ was accomplished as evidenced by the working solution color change from yellow to brown at the end of the test and consumption of hydrogen indicated by a pressure change in the reactor monitored over 1 hour. Upon completion of this test (referred to as "batch 1") the catalyst powder was recovered and the reactor was cleaned as described in the section above titled "Stirred Tank Autoclave Reactions and Apparatus". At this point the reactor was charged with the recovered catalyst minus material lost in the filtration of the working solution and in coating of the apparatus (note this powder catalyst was removed by rinsing in subsequent solvent washing of the apparatus prior to the subsequent reaction run/batch—removal of catalyst was assessed visually until not powder was visible—typically requiring about 3 liters of solvent (with a density of ~0.8 g/mL) to rinse per batch).

The reactor was then charged with a fresh 1000 mL of EAQ working solution and prepared as in the previous batch and the reaction commenced resulting in another successful hydrogenation (termed "batch 2"). Following batch 2 the same sequence was repeated for "batch 3" and "batch 4", respectively. After all four batches respectively, the catalyst powder was solvent rinsed and dried. The final weight of the catalyst was approximately 1.9 grams suggesting a loss of approximately 24% of the starting powder catalyst to filter trapping and transfer.

The EAQ conversion to $EAQH_2$ in the first batch was 28.5%. After 4 batches 297.4 g of $EAQH_2$ were deemed to be produced based on hydrogen consumption. The productivity after the first batch was 285 (based on $H_2$ moles consumed/moles Pd metal in the initial catalyst charge). Based on the process described in Sheldon, R. A., *Chem Ind*, 12-15, 1997 the E-Factor (Mass Waste g/Mass Product) of 32.6 was calculated based on grams of material waste generated (rinse and reaction solvent 12,000 mL*0.8 g/mL+ catalyst 0.6 g) and the grams of product produced over four batches.

Comparative Example 4

Approximately 2.0 grams of 2 wt % Pd by weight on a $SiO_2$—$Al_2O_3$ support—Type 429 powdered catalyst from Johnson Matthey (Royston, United Kingdom) and 1000 mL of limonene solution were charged to a Autoclave Engineers 1 gallon (~3.79 L) HASTELLOY® C vessel, model number N6657HC. A reaction was effected by pressurizing the reactor to 50 psi (~0.35 MPa) at a room temperature of 21° C. and initiating stirring at 350 rpm as described the section above titled "Stirred Tank Autoclave Reactions and Apparatus" using the standard pitched blade turbine with a metal disc stack and screens, but not including any immobilized catalyst discs described above or any PVDF screens. Reaction was accomplished as evidenced by pressure change in the reactor monitored over 1 hour. Upon completion of this test (referred to as "batch 1") the catalyst powder was recovered and the reactor was cleaned as described in the section above titled "Stirred Tank Autoclave Reactions and Apparatus".

Figure 10:
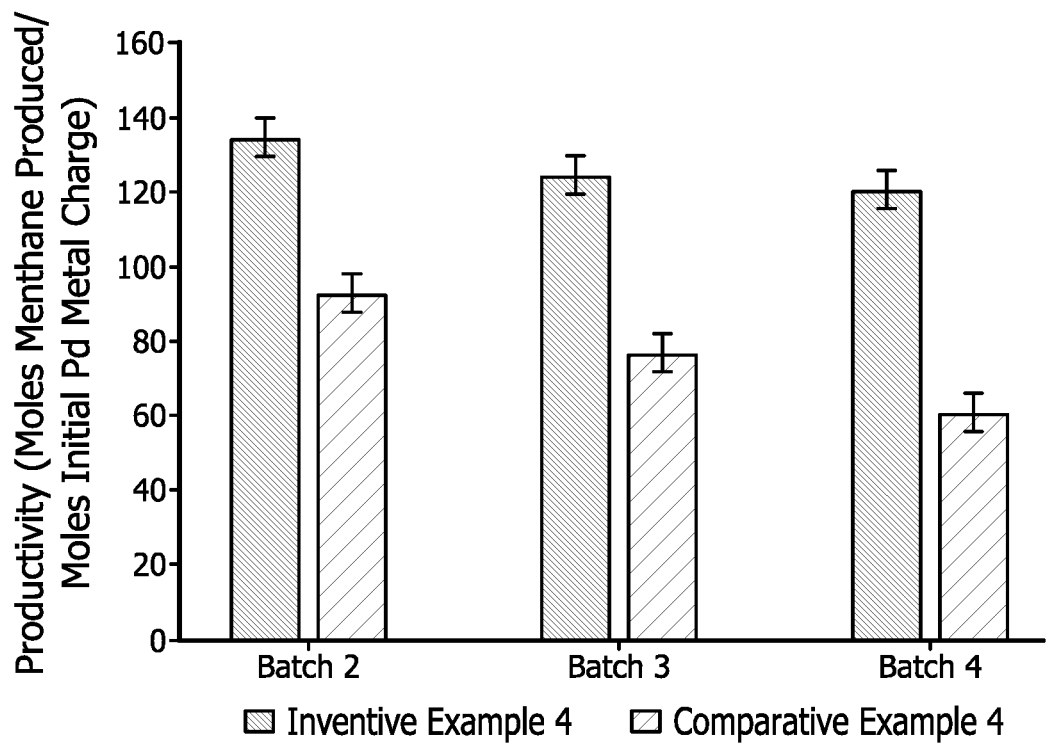
FIG. 10 is a graphical illustration of the relative productivity of batches 2, 3, and 4 of multiphase hydrogenation of hydrogen and s-limonene per moles of Pd metal charge in a stirred autoclave reactor in accordance with at least one embodiment.

The reactor was then charged with the recovered catalyst minus material lost in the filtration of the working solution and in coating of the apparatus (note this powder catalyst was removed by rinsing in subsequent solvent washing of the apparatus prior to the subsequent reaction run/batch— removal of catalyst was assessed visually until no powder was visible—typically requiring about 3 liters of solvent (with a density of ~0.8 g/mL) to rinse per batch). The reactor was then charged with a fresh 1000 mL of limonene working solution and prepared as in the previous batch and the reaction commenced resulting in another successful hydrogenation (termed "batch 2"). Following batch 2 the same sequence was repeated for "batch 3" and "batch 4", respectively. After all four batches respectively, the catalyst powder was solvent rinsed and dried). The hydrogen consumption after batches 1, 2, 3, and 4 and were measured to be 4.6 psi (~0.032 MPa), 4.5 psi (~0.031 MPa), 3.7 psi (~0.026 MPa), and 3.3 psi (~0.023 MPa); respectively. The productivity for the first batch was not used as some of the hydrogen consumed may have gone to reducing the oxidized catalyst. The productivity for the second, third, and fourth batches respectively were 94.3, 77.5, and 67.1 (based on $H_2$ moles consumed/moles Pd metal in the initial catalyst charge). FIG. 10 shows the relative productivity with the respective $2^{nd}$, $3^{rd}$, and 4th sequential batches. Based on the process described in Sheldon, R. A., 1997, supra an E-Factor (Mass Waste g/Mass Product) of 382.4 was calculated based on grams of material waste generated (rinse and reaction solvent 9,000 mL*0.8 g/mL) and the grams of product produced over four batches.

Example 1

A composite of blend of 50 wt % PTFE and 50 wt % Type 429 Pd/$SiO_2$—$Al_2O_3$ catalyst (2 wt % Pd) from Johnson Matthey (Royston, United Kingdom) having a size of approximately 14.5 μm was blended in a manner generally taught in United States Publication No. 2005/0057888 to Mitchell, et al. and subsequently uniaxially expanded according to the teachings of U.S. Pat. No. 3,953,566 to Gore. The resulting porous fibrillated ePTFE membrane included supported catalyst particles enmeshed and immobilized within the ePTFE node and fibril matrix. The porous fibrillated ePTFE membrane had a thickness of 0.47 mm. The membrane was characterized by mercury porosimetry to have an intrusion volume of 3.17 mL/g, resulting in a total porosity of 86%, a total pore area of 133.25 $m^2/g$, a bulk density of 0.27 $g/cm^3$, and a skeletal density of 1.9 $g/cm^3$. 2.33 grams of this porous fibrillated ePTFE membrane was then diced into 1 $cm^2$ squares (representing 0.0233 grams Pd metal content) and was charged into a 0.5 L Parr glass bottle with 100 mL of EAQ working solution. Hydrogenation of EAQ was successful as evidenced by the working solution changing color from yellow to brown and consumption of hydrogen that was indicated by a pressure change in the bottle of 27 psi (~0.19 MPa) following 10 minutes of agitated shaking of the catalyst powder at 50° C. The final EAQ conversion to $EAQH_2$ was 40.1%. The final productivity at termination of reaction was 400 (based on $H_2$ moles consumed/moles Pd metal).

Example 2

A composite of blend of 50 wt % PTFE and 50 wt % Type 429 Pd/$SiO_2$—$Al_2O_3$ catalyst (2 wt % Pd) from Johnson Matthey (Royston, United Kingdom) having a size of approximately 14.5 μm was blended in a manner generally taught in United States Publication No. 2005/0057888 to Mitchell, et al. and subsequently uniaxially expanded according to the teachings of U.S. Pat. No. 3,953,566 to Gore. The resulting porous fibrillated ePTFE membrane included supported catalyst particles enmeshed and immobilized within the ePTFE node and fibril matrix. The porous fibrillated ePTFE membrane had a thickness of 0.14 mm. The membrane was characterized by mercury porosimetry to have an intrusion volume of 1.04 mL/g, resulting in a total porosity of 65%, a total pore area of 68 $m^2/g$, a bulk density of 0.62 $g/cm^3$, and a skeletal density of 1.77 $g/cm^3$. The porous fibrillated ePTFE membrane comprising the supported catalyst particles was die cut into discs and assembled into a disc stack as described above in the section entitled "Formation of Disc Stack" with 16 discs and 15 PVDF spacers weighing a total of 25 grams.

The disc stack was attached to an impeller shaft, and 1000 mL of EAQ working solution were charged to a Autoclave Engineers (Parker Autoclave Engineers, Erie, Pa.) 1 gallon (~3.79 liters) HASTELLOY® C vessel, model number N6657HC. The reactor was charged to 200 psi (~1.38 MPa) and brought to a temperature of 55° C. Stirring was initiated at 350 rpm. A hydrogenation reaction was effected as described in detail in the section titled "Stirred Tank Autoclave Reactions and Apparatus" using a standard pitched blade turbine (i.e., impeller) with the disc stack affixed thereto. Hydrogenation of EAQ was accomplished as evidenced by the working solution color change from yellow to brown at the end of the test and consumption of hydrogen was indicated by a pressure change of 40.7 psi (~0.281 MPa) in the reactor monitored over 1 hour.

Following the reaction, the test fluid containing the working solution and reaction products were gravity filtered through a 0.7 μm glass fiber filter capsule (Sterlitech Corporation). To accomplish this test, a 50-mL polyethylene luer syringe barrel without plunger (Terumo Medical Corporation) was attached to the capsule and 30 mL of the catalyst slurried in the post reaction working solution was added to the barrel. Effluent from the filter capsule was collected in a 20-mL glass (class a) graduated cylinder. Volume was noted at time intervals measured by a stop watch. Results are shown in the Table and plotted in terms of flow/area per unit time or filtration flux in FIG. 8. The reactor after product recovery was visibly clean. In contrast to the non-immobilized catalyst, the filter was not clogged and continued to flow. The final EAQ conversion to $EAQH_2$ was determined to be 45%. The productivity was not calculated since the catalyst was not first preconditioned to ensure starting in a reduced state.

TABLE

| Example | Comparative Form Description | Inventive Form | System | Agitation | # of Batches considered for productivity | Comparative Example Productivity (moles product/ moles Pd) | Inventive Example Productivity (moles product/ moles Pd) | Comparative Example E Factor (g waste/ g product) | Inventive Example E Factor (g waste/ g product) |
|---|---|---|---|---|---|---|---|---|---|
| 1 | Powder | Immobilized Catalyst Pieces | EAQ | Shaken | 1 | 437 | 401 | NA | NA |
| 2 | Powder | Immobilized Catalyst Discs | EAQ | Stirred | 1 | 285 | 312 | 32.6 | 4.9 |
| 4 | Powder | Immobilized Catalyst Discs | Limonene | Stirred | 3 | 335 | 547 | 542.9 | 0.0003 |

Example 3

A composite of blend of 50 wt % PTFE and 50 wt % Type 429 Pd/SiO$_2$—Al$_2$O$_3$ catalyst was (2 wt % Pd) from Johnson Matthey (Royston, United Kingdom) having a size of approximately 14.5 μm was blended in a manner generally taught in United States Publication No. 2005/0057888 to Mitchell, et al. and subsequently uniaxially expanded according to the teachings of U.S. Pat. No. 3,953,566 to Gore. The resulting porous fibrillated ePTFE membrane included supported catalyst particles enmeshed and immobilized within the ePTFE node and fibril matrix. The porous fibrillated ePTFE membrane had a thickness of 0.47 mm. The membrane was characterized by mercury porosimetry to have an intrusion volume of 3.17 mL/g, resulting in a total porosity of 86%, a total pore area of 133.25 m$^2$/g, a bulk density of 0.27 g/cm$^3$, and a skeletal density of 1.9 g/cm$^3$. The porous fibrillated ePTFE membrane comprising the enmeshed immobilized supported catalyst particles was die cut into discs and assembled into a disc stack with die cut PVDF Scrim spacers as described above in the section entitled "Formation of Disc Stack" with 5 discs of expanded tape and 4 PVDF spacers weighing a total of 4.5 grams.

The disc stack was attached to an impeller shaft, and 1000 mL of EAQ working solution were charged to a Autoclave Engineers 1 gallon (~3.79 liters) HASTELLOY® C vessel, model number N6657HC. The reactor was charged to 200 psi (~1.38 MPa) and brought to a temperature of 50° C. A hydrogenation reaction was effected as described in detail in the section above titled "Stirred Tank Autoclave Reactions and Apparatus" using a standard pitched blade turbine (i.e., impeller) with the disc stack affixed thereto. Hydrogenation of EAQ was accomplished as evidenced by the working solution color change from yellow to brown at the end of the test and consumption of hydrogen was indicated by a pressure change of 18.7 psi (~0.129 MPa) in the reactor monitored over 1 hour.

Upon completion of this test (referred to as "batch 1") the catalyst powder was recovered and the reactor was cleaned as described in detail in the section titled "Stirred Tank Autoclave Reactions and Apparatus". The disc assembly was then rinsed with solvent (1 L to remove any hydrogenated EAQ which would form unstable peroxides on contact with air). The working solution was then filtered to capture any lost catalyst. Catalyst loss was determined to be minimal and within solvent hold up or drying changes for the filter paper (~0.01 g). The reactor was also observed to be visibly clean. The rinsed disc stack catalyst was charged to the reactor and a new 1000 mL portion of EAQ working solution and prepared as in the previous batch.

Figure 9:
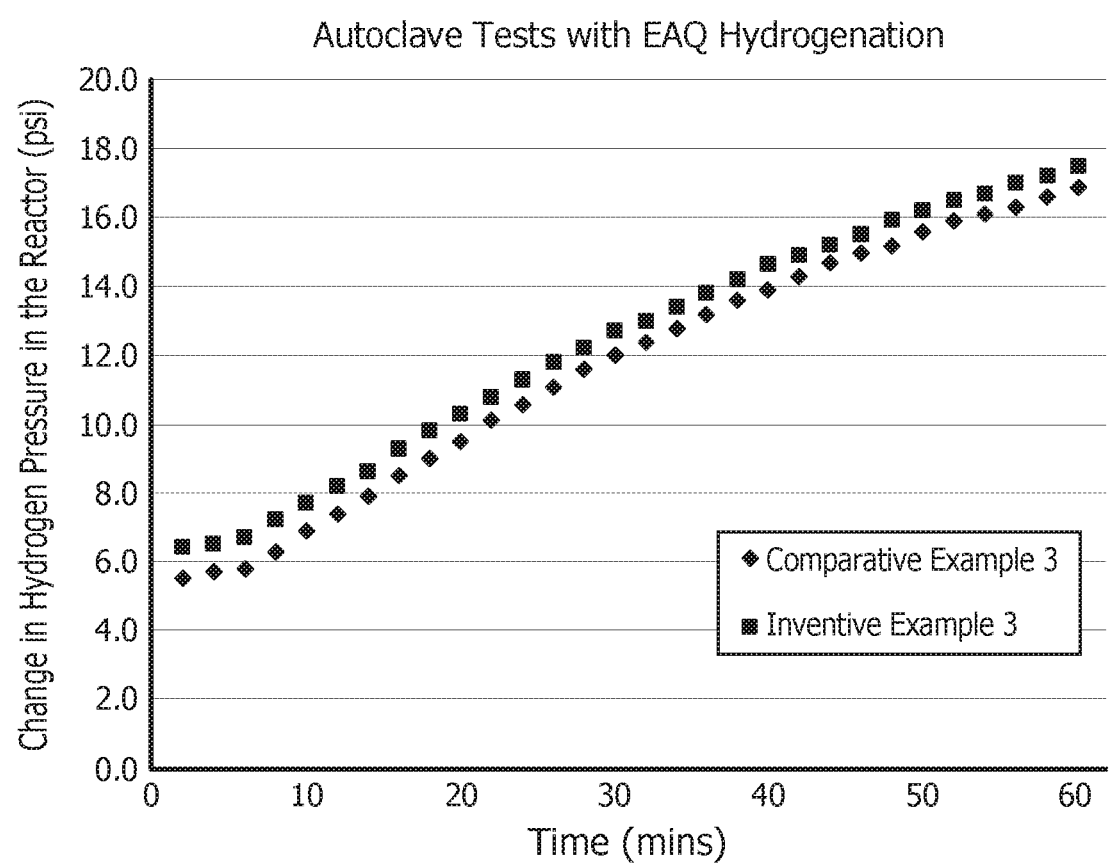
FIG. 9 is a graphical illustration of the change in pressure during autoclave reactions in accordance with at least one embodiment.

The hydrogenation reaction was then commenced resulting in another successful hydrogenation (termed "batch 2"). Following batch 2 the same sequence was repeated for "batch 3" and "batch 4", respectively (the same rinse solvent for the disc stack was used in all 4 tests). FIG. 9 shows the reactor pressure rate versus time for the first run. The EAQ conversion to EAQH$_2$ in the first batch was determined to be 31.2%. After 4 batches, 228.4 g of EAQH$_2$ were deemed to be produced based on hydrogen consumption. The productivity after the first batch was 312.4 (based on H$_2$ moles consumed/moles Pd metal in the initial catalyst charge). Based on the process described in Sheldon, R. A., 1997, supra an E-Factor of 4.7 Mass Waste g/Mass Product was calculated based on grams of material waste generated (rinse and reaction solvent 1,000 mL*0.8 g/mL) and the grams of product produced over four batches. The E factor of the immobilized structured catalyst particles is far superior to non-immobilized structured catalyst particles as demonstrated in the reduction of waste. In particular, the reduction in waste was 6.7 fold better in this Example compared to Comparative Example 3.

Example 4

A composite of blend of 50 wt % PTFE and 50 wt % Type 429 Pd/SiO$_2$—Al$_2$O$_3$ catalyst (2 wt % Pd) from Johnson Matthey (Royston, United Kingdom) having a size of approximately 14.5 μm was blended in a manner generally taught in United States Publication No. 2005/0057888 to Mitchell, et al. and subsequently uniaxially expanded according to the teachings of U.S. Pat. No. 3,953,566 to Gore. The resulting porous ePTFE membrane included supported catalyst particles enmeshed and immobilized within the ePTFE node and fibril matrix. The porous ePTFE membrane had a thickness of 0.47 mm. The membrane was characterized by mercury porosimetry to have an intrusion volume of 3.17 mL/g, resulting in a total porosity of 86%, a total pore area of 133.25 m$^2$/g, a bulk density of 0.27 g/cm$^3$, a skeletal density of 1.9 g/cm$^3$. The porous fibrillated ePTFE membrane containing immobilized catalyst was die cut into discs and assembled into a disc stack as described above in the section entitled "Formation of Disc Stack" with 5 discs weighing a total of 4.0 grams. The disc stack was then attached to an impeller shaft.

1000 mL of limonene working solution was charged to an Autoclave Engineers 1 gallon HASTELLOY® C vessel, model number N6657HC. The reactor was charged to 50 psi (~0.34 MPa) and brought to a temperature of 21° C. Stirring was initiated at 350 rpm. A hydrogenation reaction was effected as described in detail in the section above titled "Stirred Tank Autoclave Reactions and Apparatus" using a standard pitched blade turbine (i.e., impeller) with the disc stack affixed thereto. The reaction was accomplished as evidenced by pressure change in the reactor monitored over 1 hour.

Upon completion of this test (referred to as "batch 1") the catalyst powder was recovered and the reactor was cleaned as described in detail in the section above titled "Stirred Tank Autoclave Reactions and Apparatus" using a standard pitched blade turbine (i.e., impeller) with the disc stack affixed thereto. At this point the working solution with reactants and products were removed from the reactor and processed by vacuum filtration. The reactor appeared visually clean and so was deemed ready for the next batch. To accomplish reaction of the next batch the reactor was then charged with a fresh 1000 mL of limonene working solution and prepared as in the previous batch and the reaction commenced resulting in another successful hydrogenation (termed "batch 2"). Following batch 2 the same sequence was repeated for "batch 3" and "batch 4", respectively.

The recovered working solution was filtered and dried and each of the four batches. The hydrogen consumption after batches 1, 2, 3, and 4 and was 8 psi (~0.06 MPa), 6.3 psi (~0.043 MPa), 6 psi (~0.04 MPa), and 5.8 psi (~0.04 MPa), respectively. The productivity for the first batch was not used as some of the hydrogen consumed may have gone to reducing the oxidized catalyst. The productivity for the second, third, and fourth batches, respectively, were 132, 125, and 121 (based on $H_2$ moles consumed/moles Pd metal in the initial catalyst charge). FIG. 10 shows the relative productivity with across batches 2-4, respectively of this Examples versus Comparative Example 4. As shown in FIG. 10, the structured catalyst particles immobilized in the porous fibrillated polymer membrane demonstrated greater productivity than the non-immobilized structured catalysts. Based on the process described in Sheldon, R. A., 1997, supra an E-Factor (Mass Waste g/Mass product g) of 0.0006 Mass Waste g/Mass Product was calculated based on grams of material waste generated (0.01 g catalyst lost) and the 17.7 grams of product produced over four batches. The E factor of the immobilized structured catalyst particles is far superior to non-immobilized structured catalyst particles as demonstrated in the reduction of waste. In particular, the reduction in waste was 1.8 million fold better in this Example compared to Comparative Example 4.

Example 5

A composite of blend of 50 wt % PTFE and 50 wt % Type 429 Pd/SiO$_2$—Al$_2$O$_3$ catalyst (2 wt % Pd) from Johnson Matthey (Royston, United Kingdom) having a size of approximately 14.5 µm was blended in a manner generally taught in United States Publication No. 2005/0057888 to Mitchell, et al. and subsequently uniaxially expanded according to the teachings of U.S. Pat. No. 3,953,566 to Gore. The resulting porous ePTFE membrane included supported catalyst particles enmeshed and immobilized within the ePTFE node and fibril matrix. The porous fibrillated ePTFE membrane had a thickness of 0.14 mm. The membrane was characterized by mercury porosimetry to have an intrusion volume of 1.04 mL/g, resulting in a total porosity of 65%, a total pore area of 68 m$^2$/g, a bulk density of 0.62 g/cm$^3$, and a skeletal density of 1.772 g/cm$^3$. The porous fibrillated ePTFE membrane was then formed onto supported tubes, bundled, sealed in a reactor, and then inserted into the apparatus described in detail above in the section titled "Continuous Loop Reactions in a Packed Tubular Array".

The reactor apparatus was charged, prepared for reaction, and the reaction was commenced as described in "Continuous Loop Reactions in a Packed Tubular Array" set forth above. After operation for 2 hours, the concentration of EAQH$_2$ based on the titrated extracted H$_2$O$_2$ was 0.09 moles/L, corresponding to a conversion of 36% of the EAQ material with a productivity of 239. During the course of the 2 hour experiment, the working solution was recirculated through the reactor 582 times, suggesting a conversion of 0.06% per pass. This Example demonstrates that porous fibrillated polymer membrane may be used in a continuous flow reaction.

Example 6

In this example, experiments were conducted as described in Example 5 with the exception that a second tube array reactor containing the same material was added directly below the first reactor in series such that the working solution and gas bubbles flowed through the two arrays in series. After operation for 2 hours, the concentration of EAQH$_2$, based on the titrated extracted H$_2$O$_2$ was 0.16 moles/L; corresponding to a conversion of 50% of the EAQ material with a productivity of 424.

During the course of the 2 hour experiment, the working solution was recirculated through the reactor 582 times, suggesting a conversion of 0.09% per pass. This example demonstrates that the degree of hydrogenation in the flow reactor can be simply scaled or tailored to produce a product of desired conversion by the number of units in series or by altering the contact time with the immobilized supported catalyst particle. This Example demonstrates that porous fibrillated polymer membrane may be used in a continuous flow reaction in series.

Example 7

A composite of blend of 50 wt % PTFE and 50 wt % Pd/C catalyst (5 wt % Pd; Alfa Aesar PN A102023-5) was blended in a manner generally taught in United States Publication No. 2005/0057888 to Mitchell, et al. to form a PTFE/catalyst mixture and subsequently passed through calendar rolls. The resulting porous ePTFE membrane included supported catalyst particles enmeshed and immobilized within the ePTFE node and fibril matrix. The porous fibrillated ePTFE membrane had a thickness of 0.14 mm. The membrane was characterized by mercury porosimetry to have an intrusion volume of 1.04 mL/g, resulting in a total porosity of 50%, a total pore area of 120 m$^2$/g, a bulk density of 1.12 g/cm$^3$, and a skeletal density of 2.25 g/cm$^3$.

1.12 grams of the porous fibrillated ePTFE membrane was then diced into 1 cm$^2$ squares (representing 0.02818 grams Pd metal content) and then was charged into a 0.5-L Parr bottle with 100 mL of s-limonene. Hydrogenation of s-limonene was successful as evidenced by consumption of hydrogen indicated by a pressure change in the bottle of 25 psi (~110 kPa) following 10 minutes of agitated shaking of the catalyst powder at 25° C. The final limonene conversion was determined to be 4.5% (conversion was moles of product produced based on moles H$_2$ consumed based on pressure change divided by moles limonene starting material in the reactor×100). This example demonstrates that different supported catalyst particles may be enmeshed in the fibrillated polymer membrane and used in a different hydrogenation reaction.

Example 8

A composite blend of 70 wt % polytetrafluoroethylene (PTFE) and 30 wt % 5R452 Pd/C catalyst (the Pd/C supported catalyst was 5% Pd by weight) from Johnson Matthey (Royston, United Kingdom) was produced via a co-coagulation as is generally known in the art.

The composite blend material was then uniaxially expanded on a heated pantograph. The resulting expanded composite had a thickness of 0.74 mm. The expanded composite was characterized by mercury porosimetry to have an intrusion volume of 0.74 mL/g, resulting in a total porosity of 60.0%, a total pore area of 60.9 m$^2$/g, a bulk density of 0.82 g/cm$^3$, and a skeletal density of 2.04 g/cm$^3$. 0.1 grams of the expanded composite was then diced into 1 cm$^2$ squares (representing 0.05 grams Pd metal content) and was charged into a 1 L MP 06 RC1 Pressure stirred reactor with a gassing impeller (Mettler Toledo, Columbus, Ohio, USA) having a Buchiglasuster BPC pressure/hydrogen flow control and measurement system (Buchiglasuster, Uster, Switzerland) with 35 grams of nitrobenzene dispersed in 400 mL of methanol. The reactor was purged and pressurized to 3 barg (~300 kPa), set to a temperature of 30° C. using a recirculating water jacket and temperature controller. Hydrogenation of Nitrobenzene to Aniline was successful based on gas consumption measured by the BPC proportional to 0.023 moles of hydrogen at the set temperature and pressure. Following the experiments, separate GC/MS and NMR measurements confirmed Aniline had been produced in agreement with the hydrogen gas consumption.

Example 9

A composite blend of 70 wt % polytetrafluoroethylene (PTFE) and 30 wt % 5R452 Pd/C catalyst (the Pd/C supported catalyst was 5% Pd by weight) from Johnson Matthey (Royston, United Kingdom) blended in a manner generally taught in United States Publication No. 2005/0057888 to Mitchell, et al. and subsequently uniaxially expanded according to the teachings of U.S. Pat. No. 3,953,566 to Gore.

The resulting expanded composite had a thickness of 0.544 mm. The expanded composite was characterized by mercury porosimetry to have an intrusion volume of 0.84 mL/g, resulting in a total porosity of 62.2%, a total pore area of 62.1 m$^2$/g, a bulk density of 0.74 g/cm$^3$, and a skeletal density of 1.97 g/cm$^3$. 0.1 grams of this composite was then diced into 0.5 to 1 cm$^2$ squares (representing 0.05 grams Pd metal content) and was charged into a 1 L MP 06 RC1 Pressure stirred reactor with a gassing impeller (Mettler Toledo, Columbus, Ohio, USA) having a Buchiglasuster BPC pressure/hydrogen flow control and measurement system (Buchiglasuster, Uster, Switzerland) with 35 grams of nitrobenzene dispersed in 400 mL of methanol. The reactor was purged and pressurized to 3 barg (~300 kPa), set to a temperature of 30° C. using a recirculating water jacket and temperature controller. Hydrogenation of Nitrobenzene to Aniline was successful based on gas consumption measured by the BPC proportional to 0.025 moles of hydrogen at the set temperature and pressure. Following the experiments separate GC/MS and NMR measurements confirmed Aniline had been produced in agreement with the hydrogen gas consumption.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A reaction system for multiphase reactions having at least three phases, said reaction system comprising:
    a stirred tank reaction vessel comprising a rotatable impeller shaft having thereon at least one impeller blade, said rotatable impeller shaft being rotatably affixed to a catalytic article, said catalytic article comprising a porous fibrillated polymer membrane that includes supported catalyst particles durably enmeshed within the porous fibrillated polymer membrane;
    a liquid phase comprising at least one liquid phase reactant; and
    a gas phase comprising at least one gas phase reactant,
    wherein the porous fibrillated polymer membrane is in the form of an immobilized catalyst disc or disc stack.

2. The reaction system of claim 1, wherein reaction system is configured for hydrogenation.

3. The reaction system of claim 1, wherein the impeller blade is pitched.

4. The reaction system of claim 1, wherein the disc stack comprises a plurality of immobilized catalyst discs with intervening spacers separating the immobilized catalyst discs.

5. The reaction system of claim 4, wherein the immobilized catalyst discs each has therein through-holes for circulation of a reaction mixture through the disc stack.

6. The reaction system of claim 1, wherein the reaction system is a stirred tank autoclave reactor system.

7. The reaction system of claim 1, wherein the liquid phase reactant and the gas phase reactant flow across and through the catalytic article.

8. The reaction system of claim 1, wherein the porous fibrillated polymer membrane has a porosity from about 30% to about 95%.

9. The reaction system of claim 1, wherein the porous fibrillated polymer membrane is insoluble to reactants and products in the multiphase chemical reaction.

10. The reaction system of claim 1, wherein the porous fibrillated polymer membrane comprises polytetrafluoroethylene (PTFE), poly(ethylene-co-tetrafluoroethylene) (ETFE), ultra high molecular weight polyethylene (UHMWPE), polyparaxylylene (PPX), polylactic acid, and any combination or blend thereof.

11. The reaction system of claim 1, wherein the porous fibrillated polymer membrane comprises polytetrafluoroethylene (PTFE), expanded polytetrafluoroethylene (ePTFE), modified PTFE, or a PTFE copolymer.

12. The reaction system of claim 1, wherein the porous fibrillated polymer membrane comprises expanded polytetrafluoroethylene (ePTFE).

* * * * *